(12) United States Patent
Sandu et al.

(10) Patent No.: US 12,019,038 B2
(45) Date of Patent: Jun. 25, 2024

(54) EVALUATION OF SOURCE ROCK SAMPLES FROM SUBTERRANEAN RESERVOIRS

(71) Applicant: Saudi Arabian Oil Company, Dhahran (SA)

(72) Inventors: Constantin Sandu, Houston, TX (US); Shannon L. Eichmann, Katy, TX (US); David Jacobi, Houston, TX (US); Katherine Leigh Hull, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 528 days.

(21) Appl. No.: 17/154,831

(22) Filed: Jan. 21, 2021

(65) Prior Publication Data

US 2022/0228997 A1    Jul. 21, 2022

(51) Int. Cl.
*G01N 24/08* (2006.01)
*G01N 30/12* (2006.01)
(Continued)

(52) U.S. Cl.
CPC .......... *G01N 24/081* (2013.01); *G01N 30/12* (2013.01); *G01N 33/28* (2013.01); *G01R 33/3642* (2013.01); *G01N 2030/125* (2013.01)

(58) Field of Classification Search
CPC ...... G01N 24/081; G01N 30/12; G01N 33/28; G01N 2030/125; G01N 1/44; G01N 29/07;
(Continued)

(56) References Cited

U.S. PATENT DOCUMENTS

| 3,834,122 A | 9/1974 | Allison et al. |
| 4,344,917 A * | 8/1982 | Schorno ................. G01N 30/12 422/78 |

(Continued)

FOREIGN PATENT DOCUMENTS

| CN | 105784628 A * | 7/2016 |
| CN | 108152145 A * | 6/2018 |

(Continued)

OTHER PUBLICATIONS

PCT International Search Report and Written Opinion in International Appln. No. PCT/US2022/013058, dated May 11, 2022, 15 pages.

(Continued)

*Primary Examiner* — Jill A Warden
*Assistant Examiner* — Michael Paul Shimek
(74) *Attorney, Agent, or Firm* — Fish & Richardson P.C.

(57) ABSTRACT

A pyrolysis system for evaluating a source rock sample from a subterranean reservoir and methods are described. The pyrolysis system includes a reactor vessel including a body with an open end, a cover attachable to the body, a heating system, a collector assembly. The body and the cover define a sealable chamber; a source rock sample holder sized to be received inside the sealable chamber; and a sensor system. The sensor system includes a direct sensor assembly associated with the source rock sample holder, sized to be received inside the sealable chamber, and operable to measure properties of the source rock sample in the source rock sample holder; and a pyrolysis products sensor assembly in fluid communication with the collector assembly of the reactor vessel.

17 Claims, 18 Drawing Sheets

(51) Int. Cl.
*G01N 33/28* (2006.01)
*G01R 33/36* (2006.01)

(58) Field of Classification Search
CPC ......... G01N 27/023; G01N 2291/0232; G01N 33/241; G01N 31/12; G01R 33/3642
See application file for complete search history.

(56) References Cited

U.S. PATENT DOCUMENTS

| | | | |
|---|---|---|---|
| 4,485,071 | A | 11/1984 | Larter |
| 4,842,825 | A * | 6/1989 | Martin .................. G01N 31/12 422/89 |
| 4,882,128 | A | 11/1989 | Hukvari et al. |
| 5,180,556 | A | 1/1993 | Nolte et al. |
| 5,390,529 | A | 2/1995 | Ghiselli |
| 5,441,343 | A | 8/1995 | Pylkki et al. |
| 6,095,679 | A | 8/2000 | Hammiche et al. |
| 6,491,425 | B1 | 12/2002 | Hammiche et al. |
| 6,590,647 | B2 | 7/2003 | Stephenson |
| 7,078,237 | B1 * | 7/2006 | Mowry .................. G01N 31/12 436/155 |
| 7,086,484 | B2 | 8/2006 | Smith |
| 7,588,827 | B2 | 9/2009 | Nie et al. |
| 7,879,625 | B1 | 2/2011 | Boss |
| 8,177,422 | B2 | 5/2012 | Kjoller et al. |
| 8,337,783 | B2 | 12/2012 | Locascio et al. |
| 8,821,806 | B2 | 9/2014 | Hersherwitz et al. |
| 9,128,210 | B2 | 9/2015 | Pomerantz |
| 9,696,270 | B1 | 7/2017 | Roy et al. |
| 10,611,967 | B2 | 4/2020 | Inan |
| 2008/0110253 | A1 | 5/2008 | Stephenson et al. |
| 2008/0111064 | A1 | 5/2008 | Andrews et al. |
| 2010/0092865 | A1 | 4/2010 | Kanno et al. |
| 2010/0224823 | A1 | 9/2010 | Yin et al. |
| 2011/0207231 | A1 | 8/2011 | Natan et al. |
| 2011/0260051 | A1 | 10/2011 | Preudhomme et al. |
| 2011/0275061 | A1 | 11/2011 | Weidemaier et al. |
| 2012/0026037 | A1 | 2/2012 | Thomson et al. |
| 2012/0257199 | A1 | 10/2012 | Liu et al. |
| 2012/0273193 | A1 * | 11/2012 | Sen ...................... G01N 24/081 166/66.5 |
| 2013/0040292 | A1 | 2/2013 | Lopez et al. |
| 2013/0084643 | A1 | 4/2013 | Commarieu et al. |
| 2013/0259808 | A1 | 10/2013 | Chen et al. |
| 2014/0048694 | A1 | 2/2014 | Pomerantz |
| 2014/0077121 | A1 | 3/2014 | Sun et al. |
| 2014/0186939 | A1 | 7/2014 | Peterman et al. |
| 2014/0360973 | A1 | 12/2014 | Yin et al. |
| 2015/0038347 | A1 | 2/2015 | Johnson et al. |
| 2015/0079270 | A1 | 3/2015 | Wang et al. |
| 2015/0168588 | A1 | 6/2015 | Vinegar et al. |
| 2016/0341707 | A1 * | 11/2016 | Inan .................... G01N 33/241 |
| 2017/0059497 | A1 * | 3/2017 | Seltzer ............... G01R 33/3808 |
| 2017/0336528 | A1 | 11/2017 | Badri et al. |
| 2018/0134964 | A1 * | 5/2018 | Inan .................... G01N 33/241 |
| 2019/0118265 | A1 | 4/2019 | Nie et al. |
| 2021/0080413 | A1 | 3/2021 | Eichmann et al. |
| 2021/0080414 | A1 | 3/2021 | Eichmann et al. |

FOREIGN PATENT DOCUMENTS

| | | | |
|---|---|---|---|
| CN | 111380893 | | 7/2020 |
| EP | 0210845 B1 * | | 2/1987 |
| EP | 2040075 | | 3/2009 |
| GB | 2161269 | | 8/1988 |
| WO | 2010019256 | | 2/2010 |
| WO | 2014008496 | | 1/2014 |
| WO | 2014014919 | | 1/2014 |
| WO | 2015058206 | | 4/2015 |
| WO | 2016087397 | | 6/2016 |
| WO | 2017164822 | | 9/2017 |
| WO | WO 2020009981 | | 1/2020 |
| WO | WO-2020009981 A1 * | 1/2020 | ........... G01N 24/081 |

OTHER PUBLICATIONS

Van Lieshout et al., "Programmed-temperature vaporiser injector as a new analytical tool for combined thermal desorption-pyrolysis of solid samples Application to geochemical analysis." Journal of Chromatography A 764.1, Mar. 1997, 73-84, 12 pages.

Atarita et al., "Predicting Distribution of Total Organic Carbon (TOC) and S2 with Δ Log Resistivity and Acoustic Impedance Inversion on Talang Akar Formation, Cipunegara Sub Basin, West Java," Procedia Engineering, 170:, 2017, 390-397, 8 pages.

Biot et al., "Temperature analysis in hydraulic fracturing," Journal of Petroleum Technology, vol. 39, No. 11, Nov. 1987, 9 pages.

Blanz et al., "Nuclear Magnetic Resonance Logging While Drilling (NMR-LWD): From an Experiment to a Day-to-Day Service for the Oil Industry," Diffusion Fundamentals, 14(2), 2010, 5 pages.

Cahill et al., "Nanoscale Thermal Transport II," Applied Physics Reviews 1.1, 2014, 46 pages.

Cahill et al., "Nanoscale thermal transport," Journal of applied physics vol. 93, No. 2, Jan. 2003, 28 pages.

Clough et al., "Characterization of Kerogen and Source Rock Maturation Using Solid-State NMR Spectroscopy," Energy & Fuels, 29(10):, 2015, 6370-6382, 42 pages.

Ducros, "Source Rocks of the Middle East," Source Rock Kinetics: Goal and Perspectives. AAPG Geosciences Technology Workshop, Jul. 2016, 30 pages.

Esfahani et al., "Quantitative nanoscale mapping of three-phase thermal conductivities in filled skutterudites via scanning thermal microscopy," Nature Science Review, vol. 5, Issue 1, Feb. 2017, 31 pages.

Gao et al., "A Surface Functional Monomer-Directing Strategy for Highly Dense Imprinting of TNT at Surface of Silica Nanoparticles," Journal of American Chemical Society, vol. 129, No. 25, Jun. 2007, 7859-7866, 8 pages.

Hu et al., "Smart Liquid SERS Substrates based on Fe3O4/Au Nanoparticles with Reversibly Tunable Enhancement Factor for Practical Quantitative Detection," Scientific Report, vol. 4, No. 7204, Nov. 2014, 10 pages.

Klapetek, "Chapter 11: Thermal Measurements," Quantitative Data Processing in Scanning Probe Microscopy: SPE Applications for Nanometrology, 2018, 26 pages.

Lewan, "Evaluation of petroleum generation by hydrous pyrolysis experimentation," Phil. Trans. R. Soc. Lond. A, 315:, 1985, 123-134, 13 pages.

Lewan, "Experiments on the role of water in petroleum formation," Geochimica et Cosmochimica Acta, Pergamon, 61:17, 1997, 3691-3723, 33 pages.

Lu et al., "Quantitative prediction of seismic rock physics of hybrid tight oil reservoirs of the Permian Lucaogou Formation, Junggar Basin, Northwest China," Journal of Asian Earth Sciences, 178:, 2019, 216-223, 8 pages.

Mao et al., "Chemical and nanometer-scale structure of kerogen and its change during thermal maturation investigated by advanced solid-state 13C NMR spectroscopy," Geochimica et Cosmochimica Acta, 74(7):, 2010, 2110-2127, 18 pages.

Meyer et al., "Identification of Source Rocks on Wireline Logs by Density/Resistivity and Sonic Transit Time/Resistivity Crossplots," AAPG Bulletin, 68(2):, 1984, 121-129, 9 pages.

Nie et al., "Probing Single Molecules and Single Nanoparticles by Surface-Enhanced Raman Scattering," Science, vol. 275, No. 5303, Feb. 1997, 1102-1106, 6 pages.

Pollock and Hammiche, "Micro-thermal analysis: techniques and applications," Journal of Physics D: Applied Physics, vol. 34.9, 2001, 31 pages.

Rashadan et al., "Effect of the Preparation Route, PEG and Annealing on the Phase Stability of Fe3O4 Nanoparticles and Their Magnetic Properties" Journal of Experimenal Nanoscience, vol. 8, No. 2, 2013, 210-222, 14 pages.

Solomon et al., "Synthesis and Study of Silver Nanoparticles" Journal of Chemical Education vol. 84, No. 2, 2007, 332-325, 4 pages.

(56) References Cited

OTHER PUBLICATIONS

Stiles et al., "Surface-Enhanced Raman Spectroscopy," Annual Review of Analytical Chemistry, vol. 1, No. 1, Jul. 2008, 601-626, 29 pages.

Tabatabaei et al., "Well performance diagnosis with temperature profile measurements," in SPE Annual Technical Conference and Exhibition, Society of Petroleum Engineers, Oct. 30-Nov. 2, 2011, published Jan. 2011, 16 pages.

Tathed et al., "Hydrocarbon saturation in Bakken Petroleum System based on joint inversion of resistivity and dielectric dispersion logs," Fuel, 233:, Dec. 2018, 45-55, 11 pages.

Trippetta et al., "The seismic signature of heavy oil on carbonate reservoir through laboratory experiments and AVA modelling," Journal of Petroleum Science and Engineering, 177:, 2019, 849-860, 12 pages.

Yang et al., "Nanoscale geochemical and geomechanical characterization of organic matter in shale," Nature Communications, vol. 8, 2179, Dec. 19, 2017, 9 pages.

\* cited by examiner

EVALUATION OF SOURCE ROCK SAMPLES FROM SUBTERRANEAN RESERVOIRS

TECHNICAL FIELD

The present disclosure generally relates to systems and methods to evaluate a source rock sample from a subterranean reservoir, more particularly pyrolysis tools and sensing methods that can be used to evaluate the source rock sample while it is undergoing a thermal transformation.

BACKGROUND

A source rock sample may be evaluated by predicting the amount of hydrocarbon volumes originating from subsurface reservoirs using computer simulations. The computer simulations use kinetic properties of the source rock sample and organic matter (e.g., kerogen) within the geologic formations where the hydrocarbons originate. The kinetic properties of the source rock samples are determined with laboratory methods.

The laboratory methods often include hydrous pyrolysis or open system pyrolysis methods. The pyrolysis-based methods artificially heat the source rock sample and directly or indirectly measure the amount of hydrocarbons generated. Hydrous pyrolysis often includes a controlled environment within a chemical reactor under aqueous conditions simulating the natural conditions of the source rock. The open system pyrolysis approach offers an alternative by calculating real-time measurements on a small quantity of sample material.

SUMMARY

This specification describes pyrolysis tools and sensing methods that can be used to evaluate a source rock sample from a subterranean reservoir. The pyrolysis tool includes a reactor vessel, an environmental control system, a sensor system, and data acquisition and processing system (DAPS). The reactor vessel has a body with an open end and a cover attached to the body, a source rock sample holder, a heating system, and a collector assembly. The body and the cover form a sealable chamber. The source rock sample holder is inside the sealable chamber. The source rock sample holder contains the source rock sample during transformation and preserves the residual for laboratory analysis. The environmental control system includes a set of active and passive elements that regulate temperature and pressure inside the reactor vessel.

The sensor system of these pyrolysis tools includes a direct sensor assembly and a pyrolysis products sensor assembly. The direct sensor assembly is inside the sealable chamber and includes elements within the source rock sample holder. In some tools, the elements of the direct sensor assembly are disposed on or in the source rock sample itself. The pyrolysis products sensor assembly is inside the reactor vessel and is in fluid communication with the collector assembly of the reactor vessel. The sensor system includes sensors, instrumentation and signal processing circuits, receivers, transmitters, and data storing and processing devices. The sensor system acquires real-time measurement data of the source rock sample and transfers it to the DAPS system for analysis and calculations.

The devices, systems, and methods described in this specification can accurately evaluate a source rock sample during artificial maturation experiments. Specifically, the design of the reactor vessel allows measurements on the source rock sample during thermal degradation (e.g., pyrolysis) in the absence of oxygen. The reactor vessel also allows characterization and measurements of products derived from the degradation process. These measurements can be used to determine the characteristics of the source rock sample and derived products to help enhance the hydrocarbon extraction activity.

For example, the measurements can be kinetic parameters often used in computer simulations to predict the generation of hydrocarbon components during burial history. Parameters such as surrounding geothermal gradient, organic matter source, and heat flow on a regional scale can be obtained to reproduce the burial history. Using a set of kinetic parameters determined in laboratory experiments, the computer simulation approach refines the kinetic processes in the time and space domain. This allows the user to evaluate potential volumes of hydrocarbons generated considering a specific geologic scenario.

The described approach can obtain measurements on the source rock sample, kerogen, and hydrocarbons generated simultaneously with the transformation of those elements during the hydrous pyrolysis. The approach collects accurate in-situ measurements at reduced time and allows the evaluation of various samples without a large number of experimental iterations. The approach reproduces the subsurface environment accurately with a high level of details about the source rock and the hydrocarbon compositional evolution. For example, the approach provides quantitative information about the hydrocarbon compositional evolution, the source rock structure, and fluids evolution, or intermediary components that may occur during sample transformation.

In some aspects, a pyrolysis system for evaluating a source rock sample from a subterranean reservoir includes a reactor vessel including a body with an open end, a cover attachable to the body, a heating system, and a collector assembly. The body and the cover define a sealable chamber; a source rock sample holder sized to be received inside the sealable chamber; and a sensor system. The sensor system includes a direct sensor assembly associated with the source rock sample holder, sized to be received inside the sealable chamber, and operable to measure properties of the source rock sample in the source rock sample holder; and a pyrolysis products sensor assembly in fluid communication with the collector assembly of the reactor vessel.

Embodiments of a pyrolysis system for evaluating a source rock sample from a subterranean reservoir can include one or more of the following features.

In some embodiments, the direct sensor assembly is attached to or part of the source rock sample holder.

In some embodiments, the direct sensor assembly includes a magnetic induction resistivity (MIR) sensor operable to measure an electrical resistivity of the source rock sample.

In some embodiments, the direct sensor assembly includes an acoustic travel time (ATT) sensor operable to measure a length of time it takes to a sound signal to travel through the source rock sample.

In some embodiments, the direct sensor assembly includes a nuclear magnetic resonance (NMR) sensor operable to measure a radio frequency (RF) signal produced within the source rock sample.

In some embodiments, the heating system includes a heating coil incorporated in walls of the reactor vessel.

In some embodiments, the heating systems includes a thermal controller in electronic communication with the heating coil.

In some embodiments, the heating system includes a temperature probe in electronic communication with the thermal controller.

In some embodiments, a pressure control system inlet includes a pressure gauge configured to measure a pressure inside the sealable chamber.

In some embodiments, the sensor system is in electronic communication with a data acquisition and processing system (DAPS).

In some aspects, a method for evaluating a source rock sample of a subterranean reservoir includes loading the source rock sample into a source rock sample holder sized to be received inside a sealable chamber of a reactor vessel; imposing a thermal transformation on the source rock sample based on a temperature program defined by a user; acquiring a plurality of characteristic measurements from the source rock sample using a sensor system. The plurality of characteristic measurements includes acquiring a plurality of time series of temperature and hydrocarbon component production values using a direct sensor assembly; and obtaining a plurality of kinetic parameters from the temperature and the hydrocarbon component time series using a pyrolysis products sensor assembly.

Embodiments of a method for evaluating a source rock sample of a subterranean reservoir can include one or more of the following features.

In some embodiments, the method partially filling a volume with a liquid solution. An inside space of the sealable chamber defines the volume. In some cases, the method includes transferring with the liquid solution a plurality of generated products from the source rock sample to a collector assembly. In some cases, the method includes monitoring and sampling the plurality of generated products from the source rock sample with the collector assembly. In some cases, the method includes transferring heat from a heating system to the source rock sample.

In some embodiments, the method includes processing the plurality of characteristic measurements from the source rock sample using a data acquisition and processing system (DAPS).

In some embodiments, the method includes acquiring the plurality of characteristic measurements from the source rock sample by measuring an electrical resistivity of the source rock sample.

In some embodiments, the method includes acquiring the plurality of characteristic measurements from the source rock sample by measuring a length of time it takes to a sound signal to travel through the source rock sample.

In some embodiments, the method includes acquiring the plurality of characteristic measurements from the source rock sample by measuring a radio frequency (RF) signal produced within the source rock sample.

The details of one or more embodiments of these systems and methods are set forth in the accompanying drawings and the description below. Other features, objects, and advantages of these systems and methods will be apparent from the description and drawings, and from the claims.

DETAILED DESCRIPTION

This specification describes pyrolysis tools and sensing methods that can be used to evaluate a source rock sample from the subterranean reservoir. The pyrolysis tool includes a reactor vessel, an environmental control system, a sensor system, and data acquisition and processing system (DAPS). The reactor vessel has a body with an open end and a cover attached to the body, a source rock sample holder, a heating system, and a collector assembly. The body and the cover form a sealable chamber. The source rock sample holder is inside the sealable chamber. The source rock sample holder contains the source rock sample during transformation and preserves the residual for laboratory analysis. The environmental control system includes a set of active and passive elements that regulate temperature and pressure inside the reactor vessel.

The sensor system of these pyrolysis tools includes a direct sensor assembly and a pyrolysis products sensor assembly. The direct sensor assembly is inside the sealable chamber and includes elements within the source rock sample holder. In some tools, the elements of the direct sensor assembly are disposed on or in the source rock sample itself. The pyrolysis products sensor assembly is inside the reactor vessel and is in fluid communication with the collector assembly of the reactor vessel. The sensor system includes sensors, instrumentation and signal processing circuits, receivers, transmitters, and data storing and processing devices. The sensor system acquires real-time measurement data of the source rock sample and transfers it to the DAPS system for analysis and calculations.

The devices, systems, and methods described in this specification can accurately evaluate a source rock sample during artificial maturation experiments. Specifically, the design of the reactor vessel allows measurements on the source rock sample during thermal degradation (e.g., pyrolysis) in the absence of oxygen. The reactor vessel also allows characterization and measurements on products derived from the degradation process. The measurements can be used to determine characteristics of the source rock sample from subterranean reservoirs and derived products to help enhance the hydrocarbon extraction activity.

Figure 1:
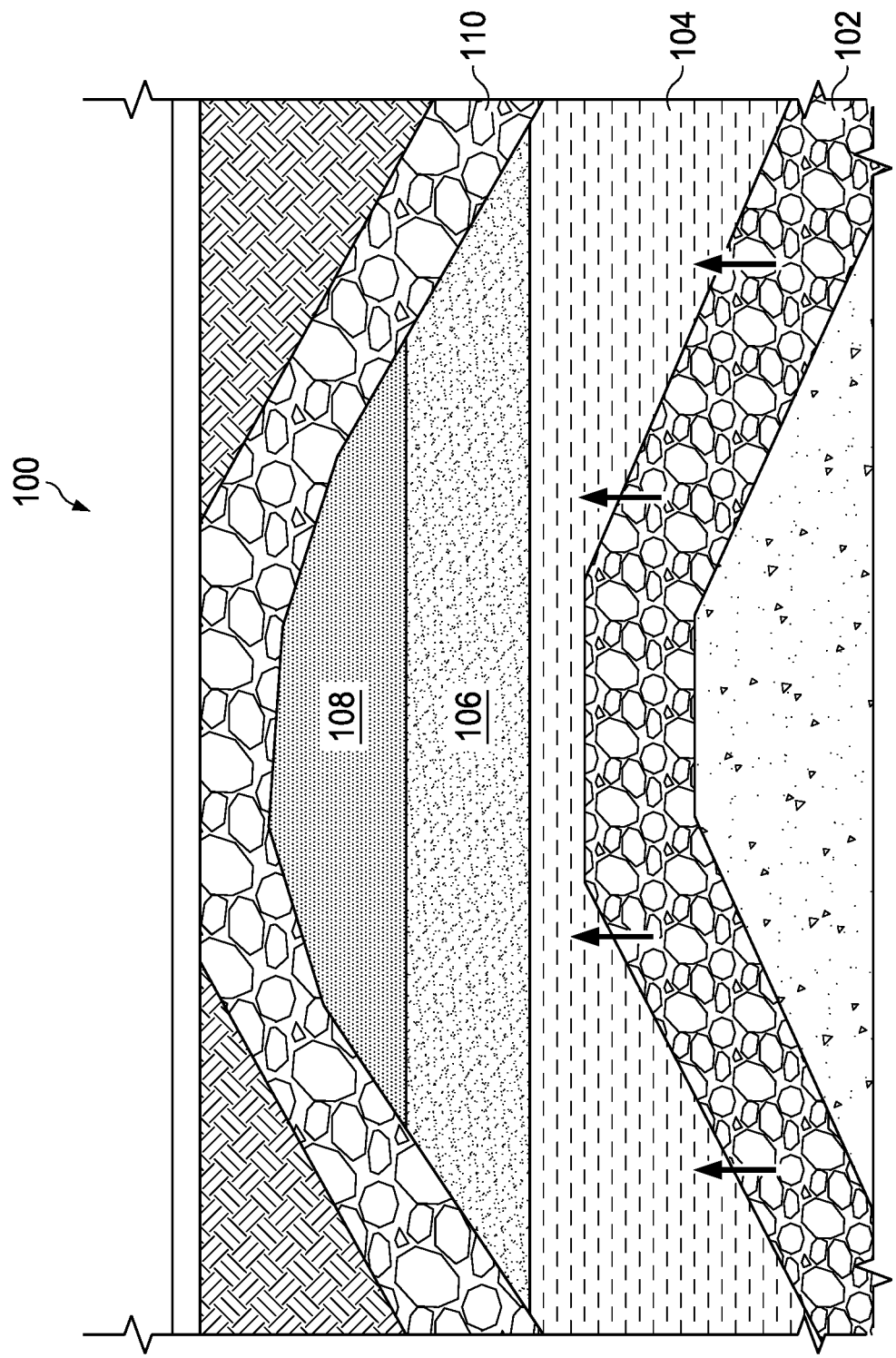
FIG. 1 is a schematic of a subterranean reservoir including source rock.

FIG. 1 is a schematic of a subterranean reservoir 100 including source rock 102. The subterranean reservoir 100 includes multiple geological layers and regions 102, 104, 106, 108, 110. The subterranean reservoir 100 includes a porous layer(s) that allows natural gas 108 to be contained within the layer(s) and to move from point to point within the layer(s). An impermeable layer 110 (e.g., caprock) overlays the porous layer(s). This impermeable layer 110 has a curved or dome-shape and prevents the gas 108 contained in the porous layer(s) from rising to the surface of the ground. It may also prevent the lateral movement of the gas 108 outside the porous layer(s). The source rock 102 is a natural sedimentary rock found in a subsurface geologic formation containing a significant amount of organic matter (e.g., approximately above 1% by mass total organic carbon). The source rock 102 undergoes various levels of thermal maturation. Artificial maturation experiments that include pyrolysis systems can be used to evaluate the source rock 102 samples from subterranean reservoirs to enhance hydrocarbon extraction activity.

Figure 2:
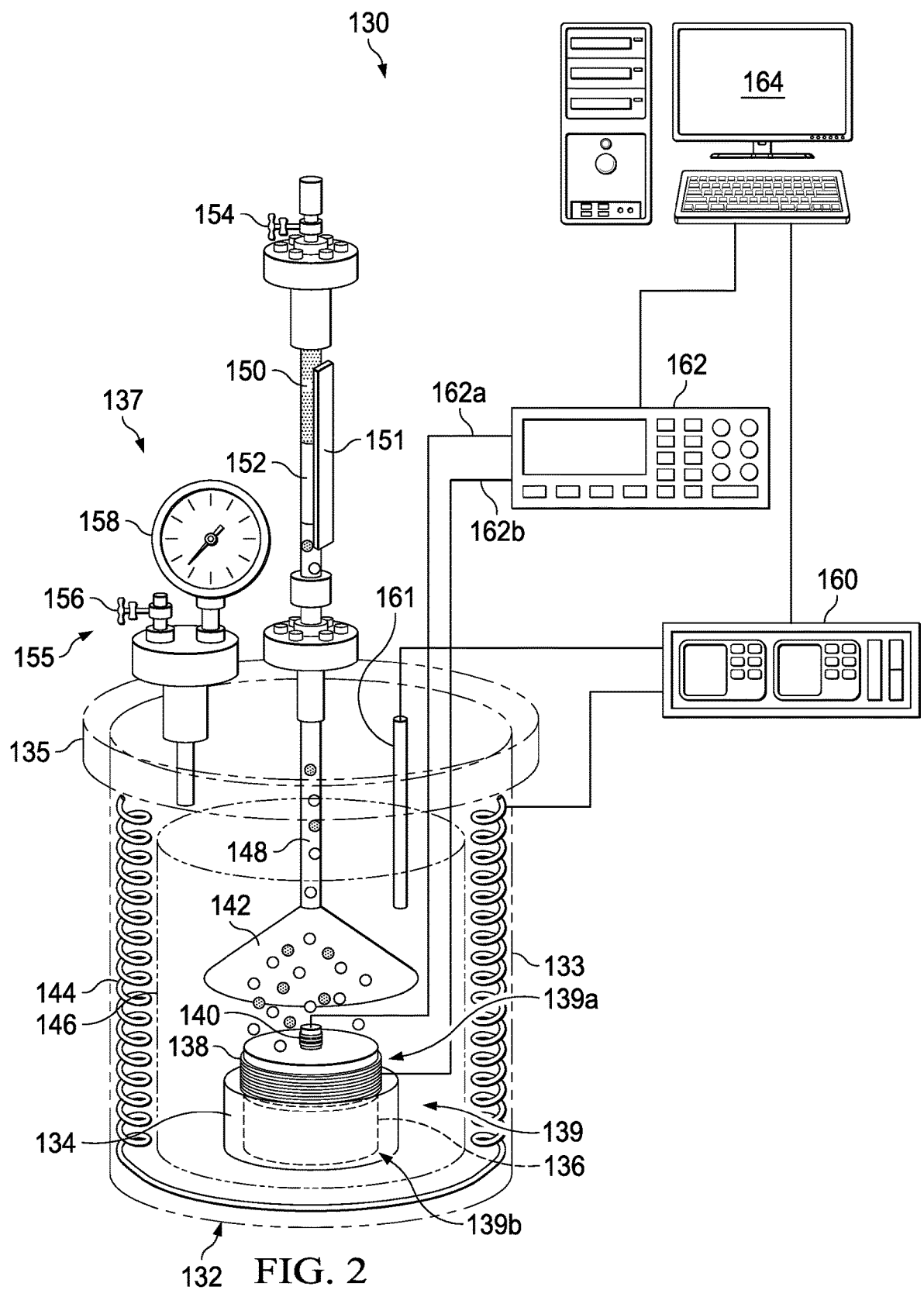
FIG. 2 is a schematic view of a pyrolysis system including a source rock sample from the subterranean reservoir.

FIG. 2 is a schematic view of a pyrolysis system 130 including a source rock sample 136 (e.g., from subterranean reservoir 100). In a subterranean reservoir, anoxic environments (i.e., oxygen-free environment) surround organic-rich sediments containing hydrogen-rich kerogens (e.g., source rock). The pores of the source rock are filled with brackish or salty water. The pyrolysis system 130 can be used for the evaluation of source rock samples during artificial maturation experiments. The pyrolysis system 130 includes a reactor vessel 132, an environmental control system 137, a sensor system 139, and data acquisition and processing system (DAPS) 164. The reactor vessel 132 can be made from metal-based material such as stainless steel or aluminum, copper, metal-based composite, or combinations of these materials. The reactor vessel 132 includes a body 133 with an open end and a cover 135 attached to the body, a source rock sample holder 134, a heating system 144, and a collector assembly 142. The body 133 and the cover 135 form a sealable chamber 146. The sealable chamber 146 maintains the anoxic environment for the source rock sample 136 under evaluation. The inner volume of the sealable chamber 146 is partially filled with a liquid solution. The liquid solution typically includes artificial seawater that closely simulates the composition of the liquid in the subsurface reservoir that fills the pores of the source rock. The liquid solution allows a transfer of generated products 148 (e.g., oil or gas) during the reaction to the collector assembly 142 for monitoring and sampling. The collector assembly 142 collects the generated products 148 and classifies them into designated oil section 152 and gas section 150 as part of the assembly 142. The collector assembly 142 includes a measurement tool 151 (e.g., ruled level scale) that measures the fluid level or collects measurements at a preset time intervals for both the oil section 152 and the gas section 150. These measurements are used for sampling analysis. The collector assembly 142 includes an outlet valve 154 positioned at an outside end. The outlet valve 154 controls the release of oil and gas from the reactor vessel 132. The liquid solution inside the reactor vessel 132 also allows a heat transfer to the source rock sample 136 from the heating system 144. The heating system 144 (e.g., a heating coil) is positioned along the inner walls of the reactor vessel 132. The heating system 144 is connected to a thermal controller 160 that allows a user to interact with the environment inside the reactor vessel 132. The heating system 144 and the thermal controller 160 are part of the environmental control system 137.

The environmental control system 137 includes additional active and passive elements that continuously interact with the environment inside the reactor vessel 132. The active and passive elements include temperature and pressure control and monitoring elements. For example, a temperature probe 161 is connected to the thermal controller 160 and measures the temperature inside the reactor vessel 132. The pressure control elements include a pressure control inlet 155 that allows access to the reactor vessel 132. The pressure control inlet 155 includes a pressure gauge 158 that measures the pressure inside the reactor vessel 132, and a control valve 156 that allows to vent off gases from the reactor vessel 132. The elements of the environmental control system 137 have the role to constrain the pressure and temperature conditions inside the reactor vessel 132 and conform to pre-assigned experimental values by the user. This enables a safe operation of the reactor vessel 132.

The reactor vessel 132 also includes the source rock sample holder 134 that is seated inside the sealable chamber 146. The source rock sample holder 134 contains the source rock sample 136 during thermal transformation and preserves the residual for experimental analysis. In some implementations, the source rock sample holder can be permanently installed in the reactor vessel, with a permanent wiring, and with a universal termination that can be connected to various sensor types. In some implementations, the source rock sample holder can be removable with one or more permanently installed sensors and a build-in wiring that connects to the sensor controllers. The source rock sample holder 134 includes elements from the sensor system 139 that allow real-time data acquisition of the source rock sample 136 and the product's parameters generated from the pyrolysis process. The sensor system 139 includes a direct sensor assembly 139a that is associated with the source rock sample holder 134 inside the sealable chamber 146. The direct sensor assembly 139a measures properties of the source rock sample 136 placed onto the source rock sample holder 134. The sensor system 139 also includes a pyrolysis products sensor assembly 139b that communicates with the collector assembly 142 of the reactor vessel 132 via the liquid solution. The direct sensor assembly 139a can be attached to or part of the source rock sample holder 134. For example, a receiver coil 140 is inside the source rock sample 136 and an emitter coil 138 is placed partially around the circumference of the source rock sample 136. The set of coils 138, 140 are in connection to a sensor controller 162 via leads 162a and 162b. The set of coils 138, 140 allow electromagnetic measurements to be performed on the source rock sample 136 and the products of the pyrolysis reaction in real-time. The sensor controller 162 receives the measurements from the set of coils 138, 140 in the form of electrical current, and converts the signal into measurement data. The sensor controller 162 communicates with DAPS 164 to transfer the measurement data for analysis and calculations.

Figure 3:
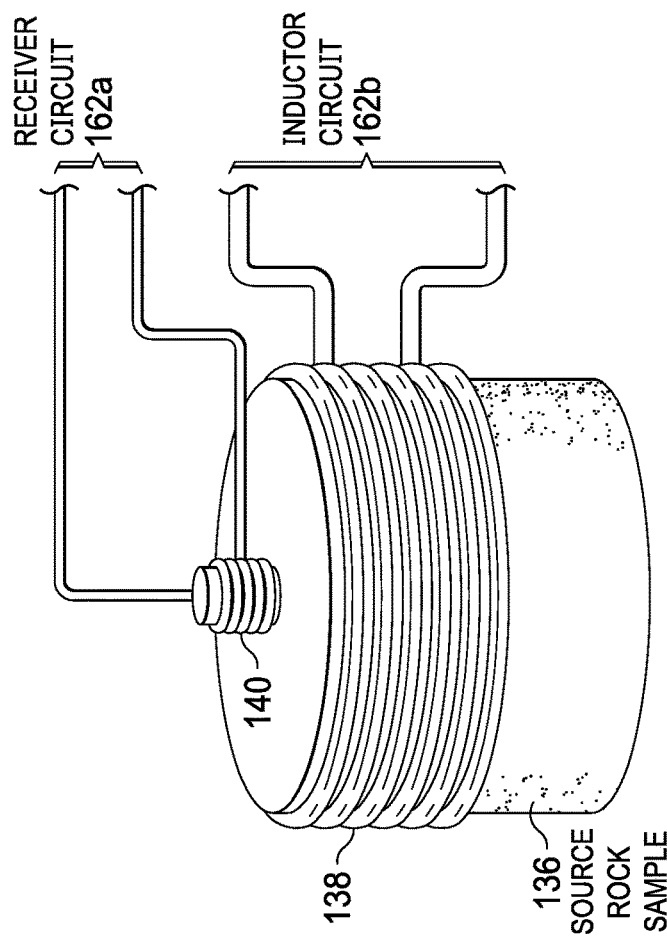
FIG. 3 is a schematic view of a source rock sample with a direct sensor assembly with a magnetic induction resistivity-based sensor.

FIG. 3 is a schematic view of a source rock sample 136 with a direct sensor assembly 139a with a magnetic induction resistivity (MIR)-based sensor. The MIR sensor measures the electrical resistivity of the source rock sample 136. The receiver coil 140 inside the source rock sample 136 and an emitter coil 138 placed partially around the circumference of the source rock sample 136 are the main components of the direct sensor assembly 139a with the magnetic induction resistivity (MIR)-based sensor. The set of coils 138, 140 induce and receive an electric signal from the source rock sample 136, respectively.

Figure 4:
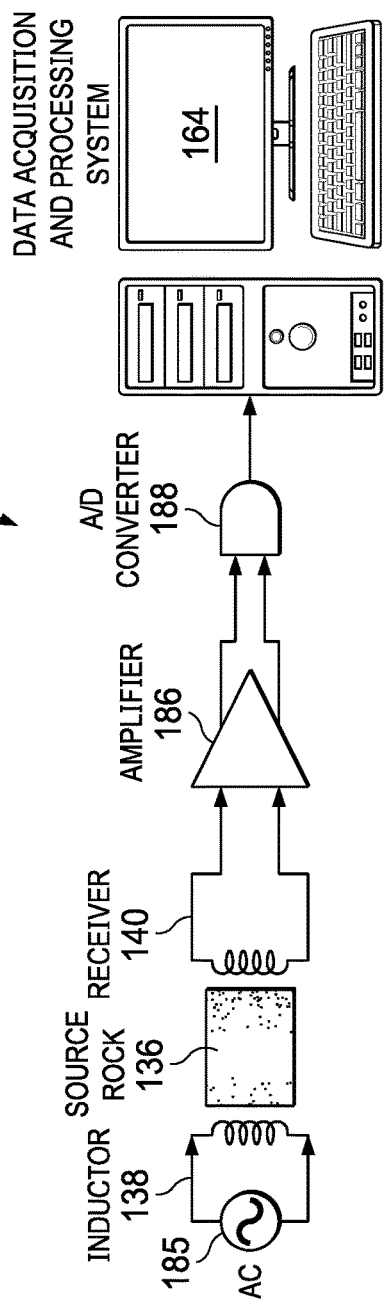
FIG. 4 is a schematic diagram of a direct sensor assembly with magnetic induction resistivity-based sensing components.

FIG. 4 is a schematic diagram 184 of a direct sensor assembly 139a with a magnetic induction resistivity-based sensing components. Diagram 184 shows an electrical circuit functionality of the direct sensor assembly 139a with magnetic induction resistivity-based sensing components. The magnetic induction resistivity sensing operates by application of a high-frequency alternating current (AC) applied to an emitter coil that generates a varying magnetic field near the sample under evaluation. In this example, the AC 185 is applied to induction coil 138 that is placed around the circumference of source rock sample 136. The induction coil 138 induces a secondary current into the source rock sample 136 through a varying magnetic field. The generated magnetic field from the source rock sample 136 is detected by the receiver coil 140. The magnitude of the received signal is proportional to the intensity of the induced current and evaluates the electrical conductivity of the source rock sample 136. The detected signal is amplified with an amplifier 186 and converted with a converter 188 to digital information received by DAPS 164 for analysis. Electrical resistivity and reciprocal electrical conductivity are parameters related to the ability of a sample to conduct electricity. As the source rock sample maturation progresses, hydrocarbons are generated from the organic matter disseminated within the source rock. The hydrocarbons progressively occupy the pore space displacing the interstitial saltwater saturated in the sample at the beginning of the experiment. This effect is detected by the induction resistivity sensor and converted to an electrical signal for analysis.

Figure 5:
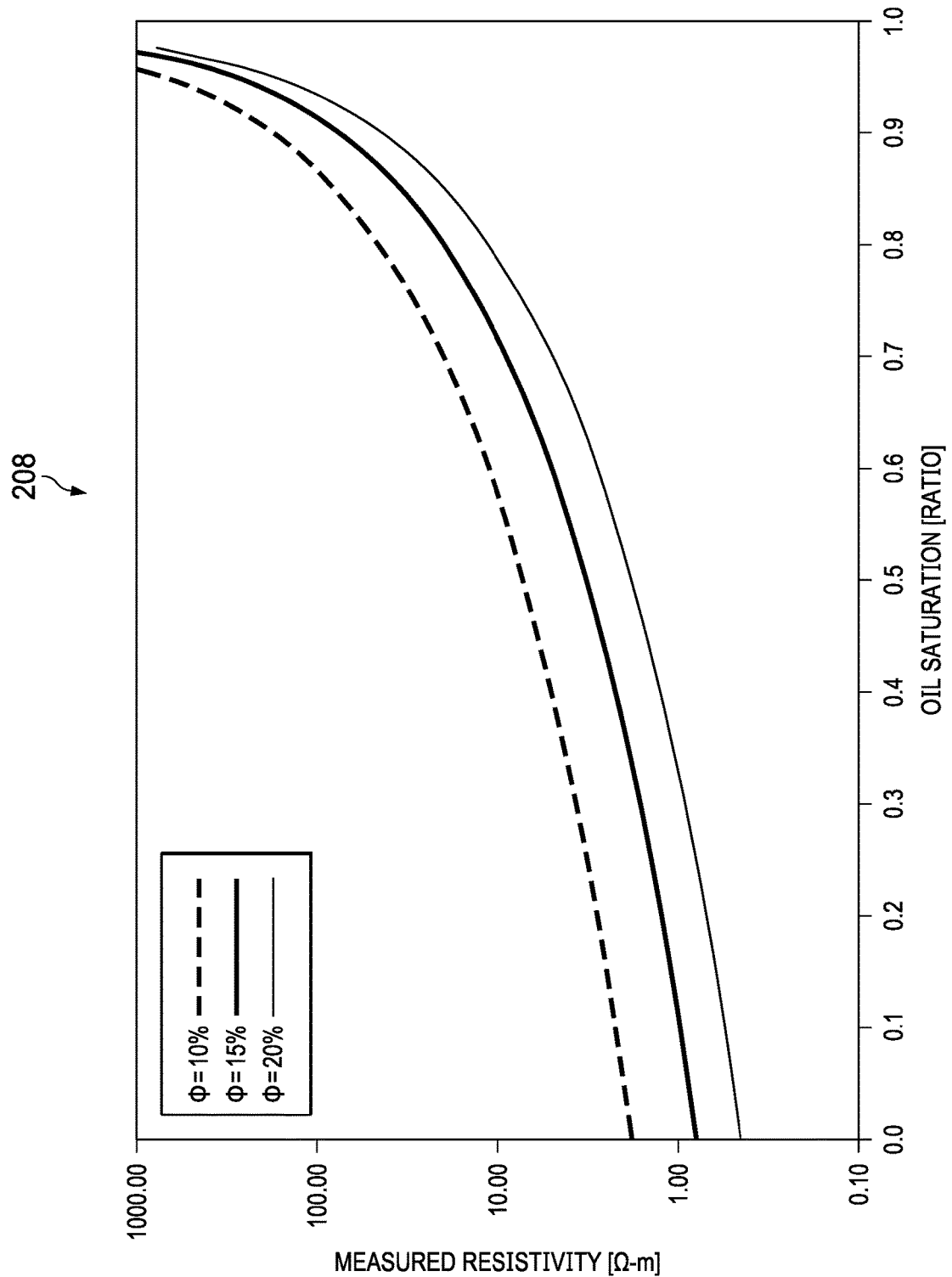
FIG. 5 is an example chart of a measured resistivity of a source rock sample.

FIG. 5 is an example chart 208 of a measured resistivity of a source rock sample 136. Chart 208 shows a set of simulations for the data generated from the resistivity measurement sensor for the increasing hydrocarbons saturation inside the source rock sample pores. The simulations are calculated using the Archie Equation (Eq.1):

$$S_w^n = \frac{R_w}{(\phi^m \times R_t)} \quad \text{Eq. (1)}$$

where $S_w$ is water saturation of an uninvaded zone, n is a saturation exponent, $R_w$ is formation water resistivity at formation temperature, $\phi$ is porosity, m is cementation exponent, and $R_t$ is true resistivity of the formation. The calculations from Equation 1 represent the empirical relationship between the source rock properties, water, and hydrocarbon saturation, and apparent resistivity applied on the samples with known porosity. The three curves in FIG. 5 each represent a simulation result for different porosity (e.g., 10%, 15%, and 20%) of a source rock sample. The results show the higher porosity in the sample results in higher contrast of resistivity between water-saturated and hydrocarbons-saturated pore space.

Figure 6:
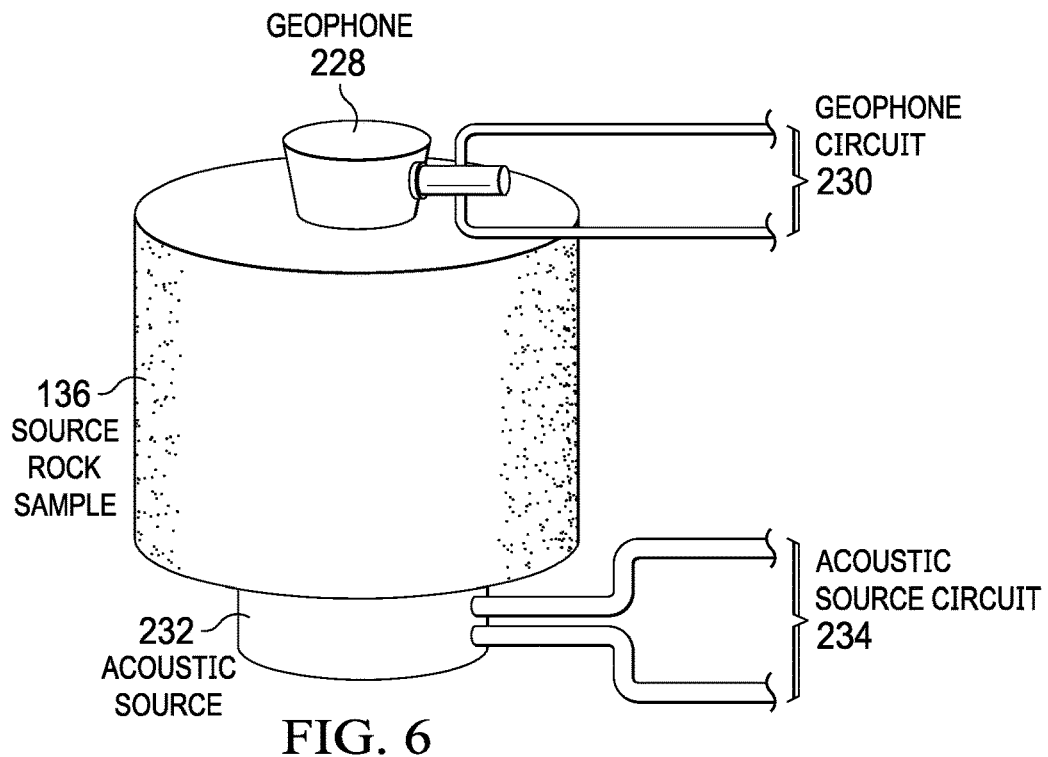
FIG. 6 is a schematic view of a source rock sample with a direct sensor assembly with an acoustic travel time-based sensor.

FIG. 6 is a schematic view of a source rock sample 136 with a direct sensor assembly 139a with acoustic travel time (ATT)-based sensor. The ATT sensor measures the length of time it takes for a sound signal to travel through a source rock sample. The main components of the direct sensor assembly 139a are the acoustic source 232 and the geophone 228. The acoustic source 232 and the geophone 228 are placed inside the source rock sample 136.

Figure 7:
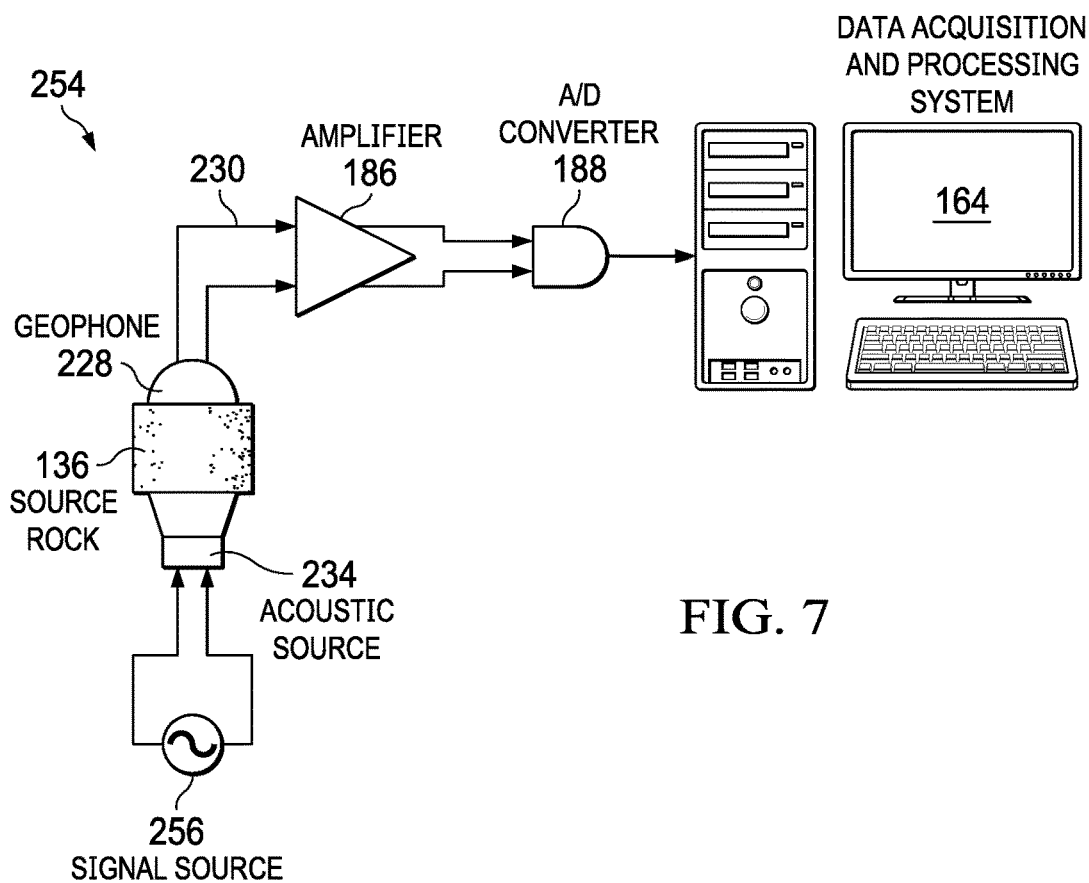
FIG. 7 is a schematic diagram of a direct sensor assembly with acoustic travel time-based sensing components.

FIG. 7 is a schematic diagram 254 of a direct sensor assembly 139a with an acoustic travel time-based sensing components showing the ATT sensor being used for evaluation of the source rock sample 136. An electrical signal is generated by the signal source 256 and converted to an acoustic signal by the acoustic source 232. The acoustic signal is applied on one side of the source rock sample 136 and it transits through the sample then the geophone 228 receives the signal on the other side of the source rock sample 136. In one example, the ATT sensor is connected to a sensor controller 162 that can include an integrated processor. The integrated processor can measure the length of time for the signal being fired by the acoustic source 232 and received by the geophone 228. The acoustic velocity is different between the generated hydrocarbons and original interstitial water. During the maturation experiment of the source rock, as the hydrocarbons progressively displace water the travel time of the sound changes. Specifically, since the hydrocarbons present a more rigid environment than the displaced water, the travel time of the sound signal increases linearly with the hydrocarbon saturation.

Figure 8:
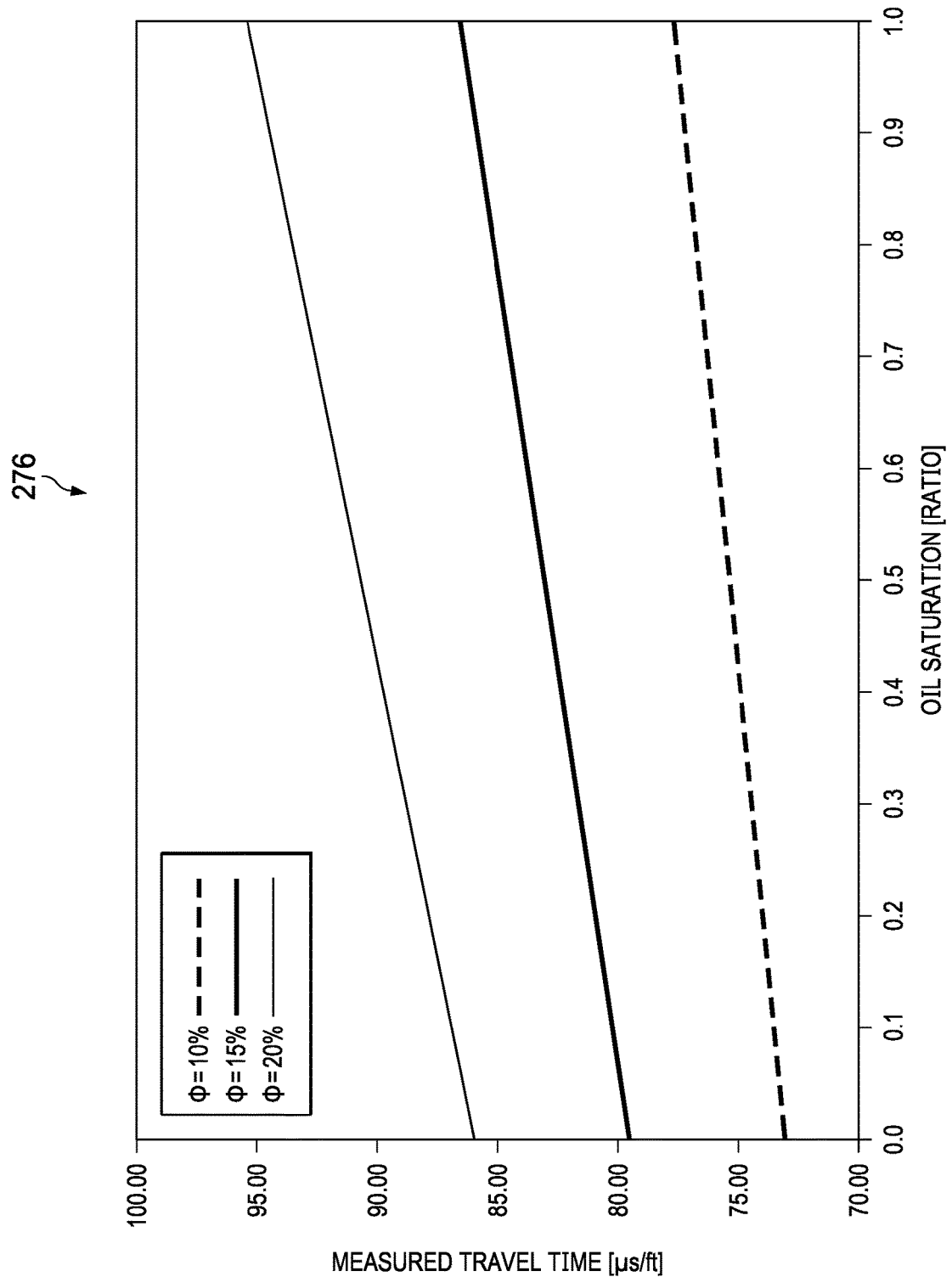
FIG. 8 is an example chart of a measured travel time of a sound signal through a source rock sample.

FIG. 8 is an example chart 276 of a measured travel time of a sound signal through a source rock sample 136. The distribution chart 276 shows a set of simulations for the measured travel time of a signal through the source rock sample using the ATT sensor as the sample undergoes thermal aging. Chart 276 shows as the hydrocarbons saturation increases in the sample pore the signal travel time increases linearly. The simulations are based on the Wyllie time-average equation that empirically relates the acoustic velocity of a porous rock to the properties of the rock matrix and fluids present within the pores, applied on samples with known porosity. The three curves each represent a simulation result for different source rock sample porosity. The higher the porosity results in a larger contrast of travel time between water-saturated and hydrocarbons saturated pore space.

Figure 9:
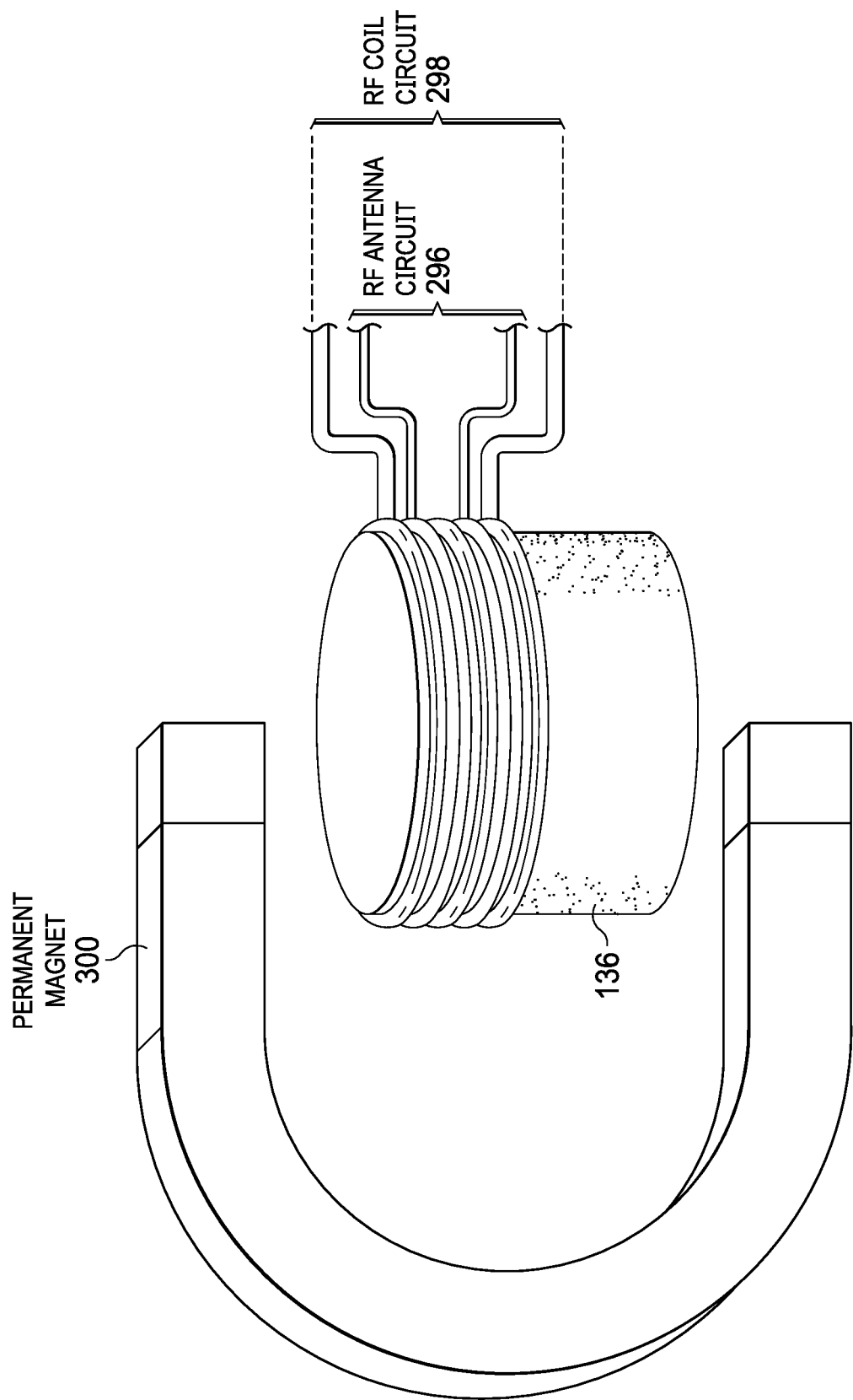
FIG. 9 is a schematic view of a source rock sample with a direct sensor assembly with a magnetic resonance-based sensor.

FIG. 9 is a schematic view of a source rock sample 136 with a direct sensor assembly 139a with a nuclear magnetic resonance (NMR)-based sensor. The NMR sensor measures the Radio Frequency (RF) signal produced by a cycle of magnetic perturbation/relaxation acting upon the hydrogen atoms composing the water and hydrocarbons present within the source rock sample. Based on the intensity and other parameters of the RF signal the state of the source rock maturity is evaluated. In this example, the main components of the NMR direct sensor assembly 139a are a permanent magnet 300, an RF coil circuit 298, and an RF antenna circuit 296. The permanent magnet 300 has a U-shape and partially encloses the source rock sample 136. The RF coil circuit 298 and the RF antenna circuit 296 are connected with the sensor controller 162.

Figure 10:
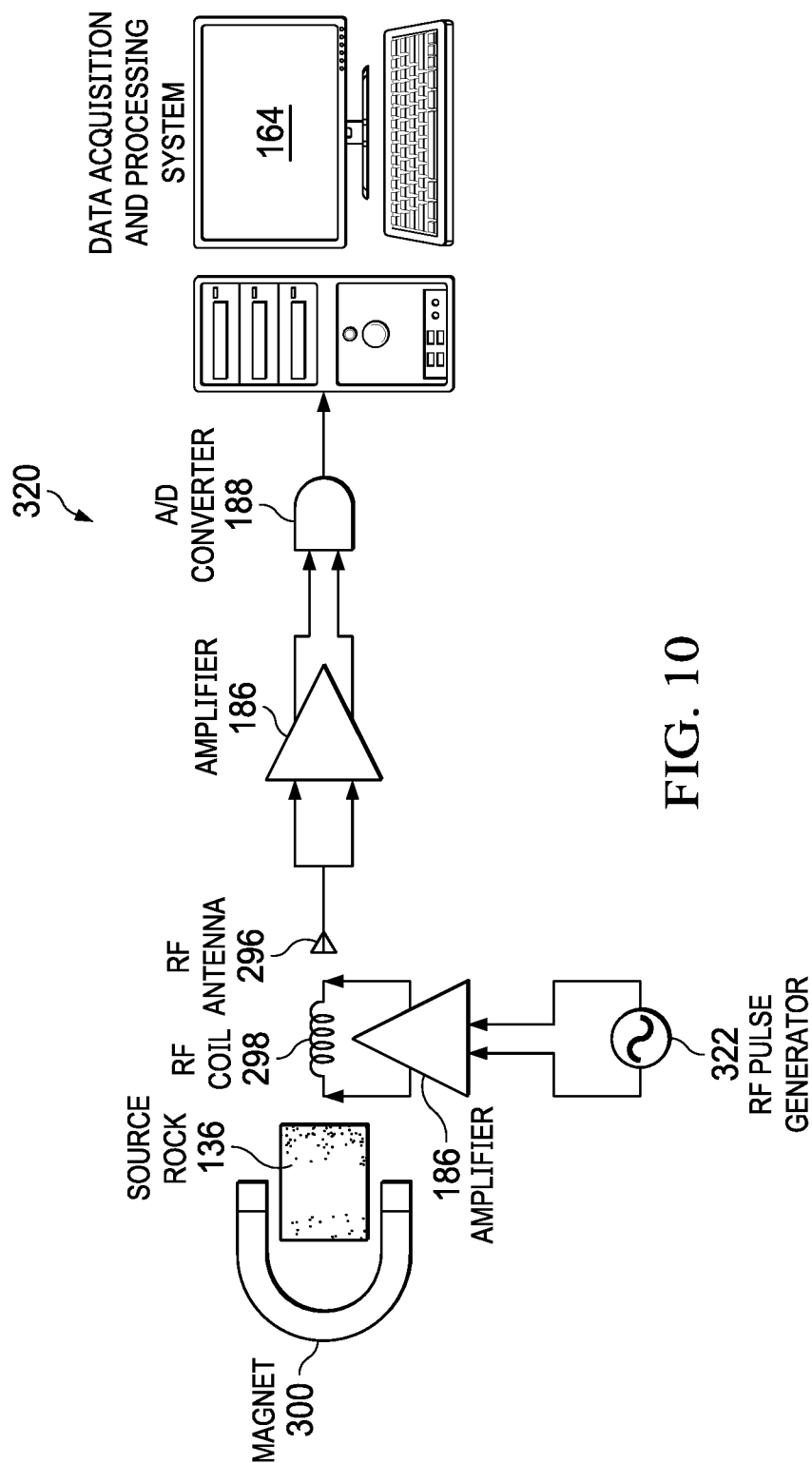
FIG. 10 is a schematic diagram of a direct sensor assembly with magnetic resonance-based sensing components.

FIG. 10 is a schematic diagram 320 of a direct sensor assembly 139a with magnetic resonance-based sensing components. A permanent magnet 300 is used to apply a magnetic field on the source rock sample 136. The magnetic field aligns the spins of hydrogen nuclei of the interstitial fluids within sample 136 to the permanent magnetic field. An electrical signal is generated by the RF pulse generator 322, and after being amplified with amplifier 186 it is applied to the RF coil 298. The RF signal generated creates a pulsating magnetic field over source rock sample 136 which disturbs the nuclei with the aligned spin. Between the induced pulses, the spin relaxation generates a response RF signal that is conditioned by the properties of the interstitial fluids within the sample pores. More specifically, the response signal is fading away in time with a characteristic relaxation time. The relaxation time depends on the content and volume of the hydrogen-containing fluids in the pore space. The received signal is amplified and transferred to the DAPS 164 after conversion to digital format. A series of relaxation times coming from various atomic sources are recorded and processed by the DAPS 164.

Figure 11:
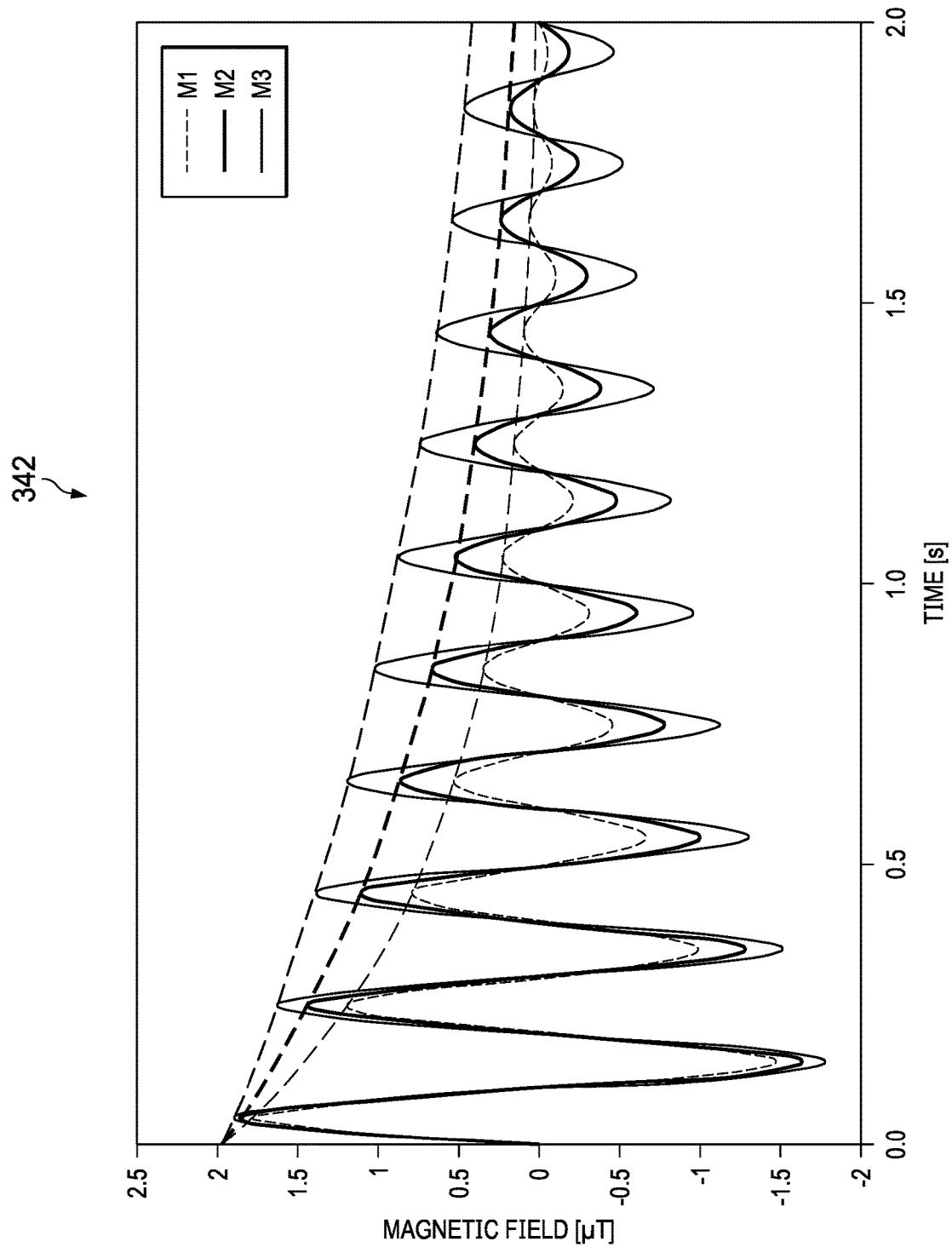
FIG. 11 is an example chart of measured magnetic fields at different sources within a source rock sample.

FIG. 11 is an example of distribution curves of measured magnetic fields at different sources within a source rock sample 136. Chart 342 presents a set three of simulations for the MRL sensor measurement response for various content of the pore space. The attenuation curve, marked with an interrupted line for each relaxation signal (e.g., M1, M2, M3) is different for each location and type of content within the hydrogen bearing fluids in the source rock sample 136. A multitude of relaxation time can be obtained based on the configuration of the sensor controller in a predefined series. The series of relaxation times are convoluted by DAPS 164 to create signal envelopes for fluid and pore typing analysis. Based on the NMR data processed, the content of hydrocarbons generated can be determined.

Figure 12:
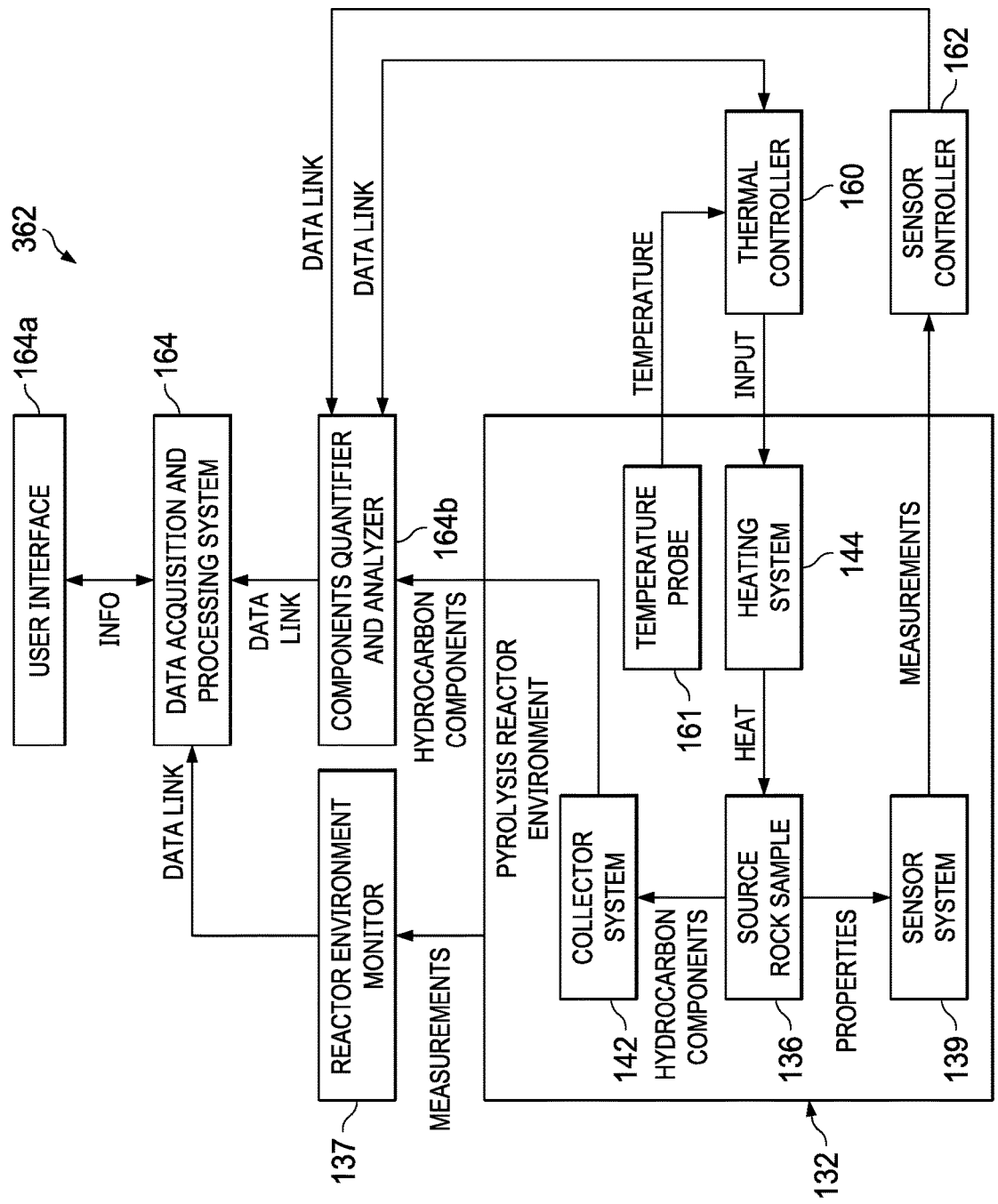
FIG. 12 is a flow chart showing a relationship between components in the pyrolysis system.

FIG. 12 is a flow chart 362 showing a relationship between components in the pyrolysis system. The components in the pyrolysis system act in synchronized mode to enable continuous evaluation of the source rock sample and monitoring of generated products during the maturation experiment. As shown in chart 362, the real-time communication between components allows measurements to be obtained and adjusted during the thermal maturation of the source rock sample. In this example, the flow chart 362 shows one example of the layout of the main components as well as the relationships between them. At the start of the maturation experiment, the DAPS 164 allows coordination between components for control and data acquisition. The thermal controller 160 activates the heating system 144 that maintains and changes the temperature according to a pre-defined program or user commands stored in DAPS 164. The thermal controller 160 is connected to a temperature probe 161 placed inside the reactor vessel 132. The reactor vessel 132 maintains a feedback loop between the heating system 144 and the thermal controller 160. As the maturation experiment progresses, the source rock sample 136 undergoes a physical transformation. The sample transformation is sensed by the sensor system 139 and reported to the sensor controller 162. Simultaneously, the products 148 (e.g., hydrocarbon and nonhydrocarbon components) generated during the source rock transformation are collected by a collector system 142, and their amount is quantified by the components quantifier and analyzer unit 164b. The measurements obtained from the source rock sample 136 by the sensor system and the measurements from the generated products 148 are reported to the DAPS 164 through each component data link. The DAPS 164 stores the data for integration and analysis. The environmental control system 137 regulates the environment within the reactor vessel 132. The environmental control system 137 obtains continuous measurements of the environment. In some examples, the measurements can be sent to DAPS 164 for storage or to initiate an action by a user and by the DAPS 164 for other components within the system. In some examples, a user interface 164a can be implemented into the pyrolysis system. The user interface 164a can receive commands and report data to a user. In other examples, some of the components present in this chart 362 can be removed or rearranged.

Figure 13:
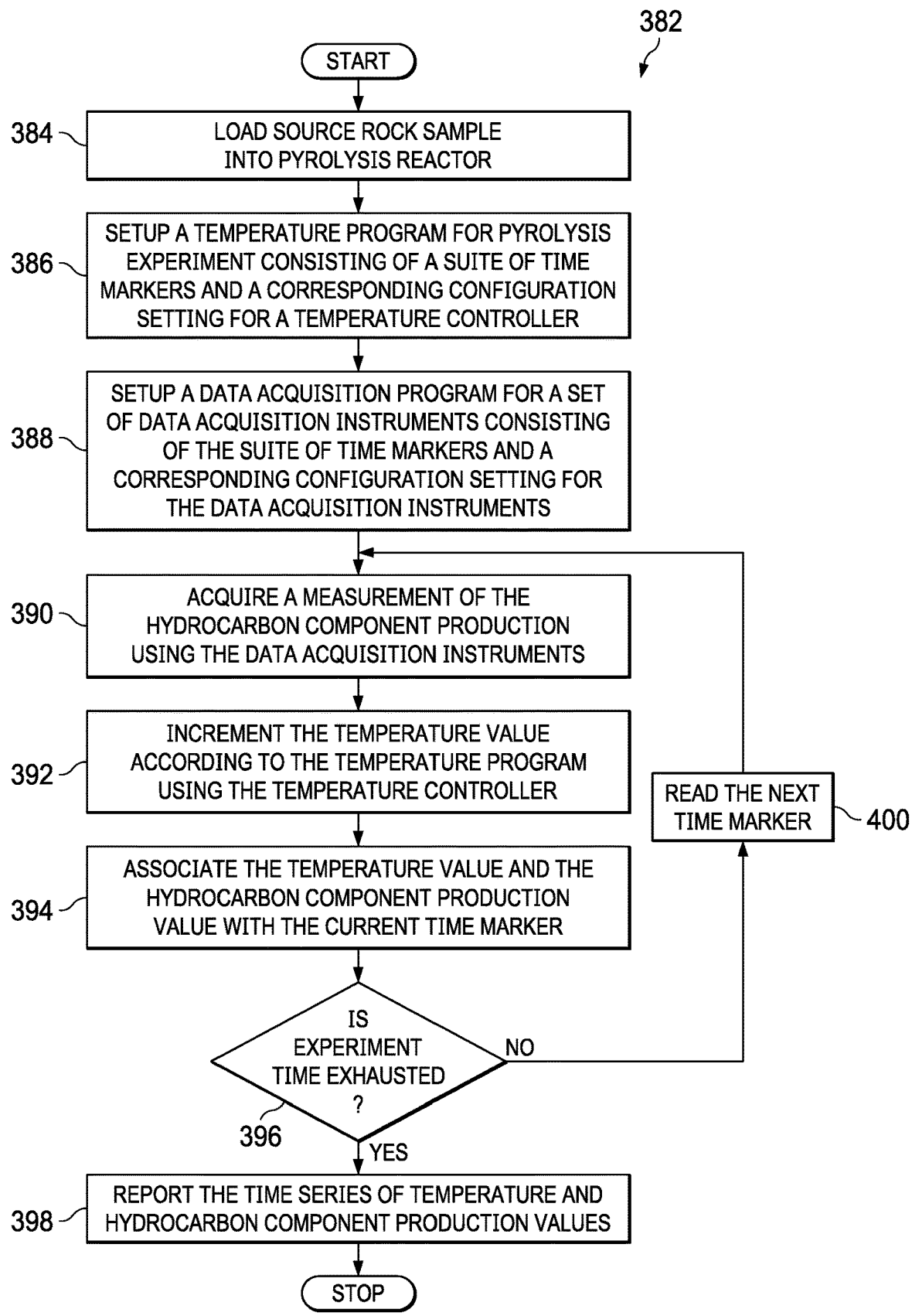
FIG. 13 is a flow chart showing a workflow for acquiring time series production values using a direct sensor assembly.

FIG. 13 is a flow chart 382 showing a workflow for acquiring time series production values using a direct sensor assembly 139a. At step 384, the source rock sample 136 is loaded into the reactor vessel 132 specifically, it is placed into the source rock sample holder 134. The reactor vessel 132 is filled with the liquid solution (e.g., artificial seawater) and it is closed and sealed. At step 386, a temperature program for the maturation experiment is defined within the DAPS 164 by a user. The temperature program includes a suite of time markers and a corresponding configuration setting for a temperature controller 160. The temperature program initiates tasks in the temperature controller 160 to attain and maintain a predefined temperature value inside the reactor vessel 132. At step 388, a data acquisition program is defined within the DAPS 164. The data acquisition program includes a suite of time markers and a corresponding configuration setting for one or more sensor systems, components quantifier, and analyzers, or environmental monitoring (e.g., data acquisition instruments). The data acquisition program initiates tasks on the data acquisition instruments that result in parameters measured and data sent to the DAPS 164. At step 390, a measurement of the hydrocarbon component production is acquired using the data acquisition instruments. At step 392, the temperature value is adjusted to a level according to a pre-defined temperature program using the temperature controller 160. At step 394, the DAPS 164 associates a temperature value and the measured hydrocarbon component production value with the current time marker. At step 396, if the experiment time defined in the temperature program or data acquisition program is not exhausted, a new measurement of hydrocarbon production is requested from the data acquisition instruments (step 400) and the workflow returns to step 390. In event that the experiment time is exhausted (step 398), the time series of temperature and hydrocarbon component production values are reported to the user or saved to a data repository within the DAPS 164. Based on the time series production values obtained in this workflow, the described systems and methods additionally aim to evaluate characteristics of the sampled source rock that can be used in oilfield production development. For example, a plurality of kinetic parameters can be derived based on the time series collected of the source rock sample for the hydrocarbon components. The kinetic parameters can be used to predict the potential volume of oil in an oilfield.

Figure 14:
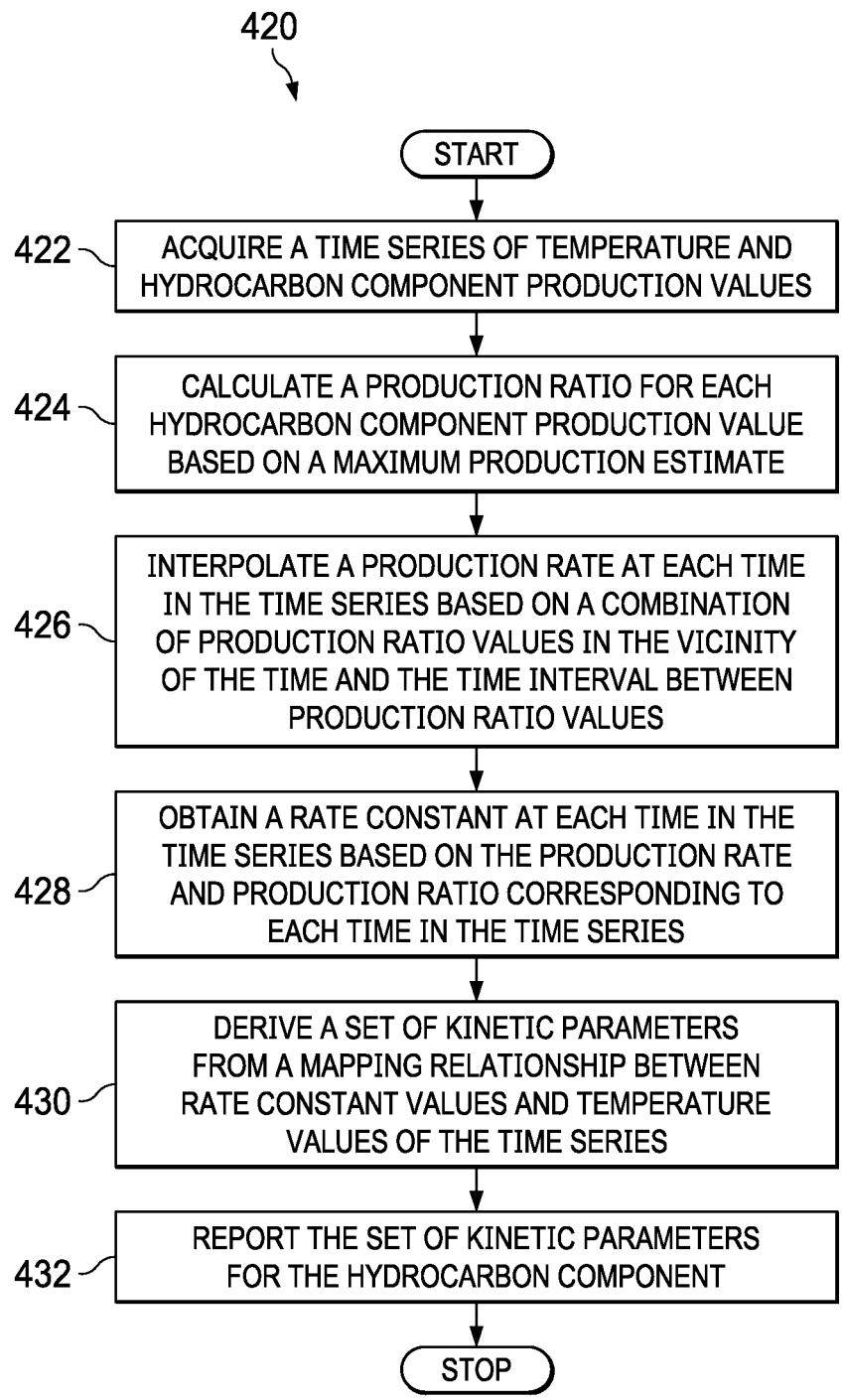
FIG. 14 is a flow chart showing a workflow for obtaining a plurality of kinetic parameters from the time series values obtained in FIG. 13 using a pyrolysis product sensor assembly.

FIG. 14 is a flow chart 420 showing a workflow for obtaining a plurality of kinetic parameters from the time series values from FIG. 13 using a pyrolysis product sensor assembly. At step 422, a time series of temperature and hydrocarbon component production values are acquired following the workflow described in FIG. 13. At step 424, a production ratio (Y) for each hydrocarbon component production value (P) is calculated based on a maximum production estimated value ($P_{max}$) at the end of the experiment using Equation 2:

$$Y = P/P_{max} \qquad \text{Eq. (2)}$$

At step 426, a production rate at each time in the time series is derived by interpolation based on a combination of production ratio values in the vicinity of the time and the time interval between production ratio values using Equation 3:

$$dY(t)/dt = [Y(t+\Delta t) - Y(t)]/\Delta t \qquad \text{Eq. (3)}$$

At step 428, a rate constant is obtained at each time in the time series based on the production rate and production ratio corresponding to each time in the time series. For a reaction, X⇒Y and k=rate constant, the production rate is:

$$dY(t)/dt = -dX(t)/dt = k \cdot X(t) \qquad \text{Eq. (4)}$$

From mass conservation, a production rate is calculated using Equation 5:

$$Y(t) = 1 - X(t) \to dY(t)/dt = k(1-Y(t)) \qquad \text{Eq. (5)}$$

The rate constant is obtained using Equation 6:

$$k = [dY(t)/dt] * [1/(1-Y(t))] \qquad \text{Eq. (6)}$$

At step 430, a set of kinetic parameters is derived from a mapping relationship between the rate constant values and the temperature values of the time series using equations 1 and 2. At step 432, the process is terminated and the set of kinetic parameters for the hydrocarbon component is reported.

In summary, the steps of flow chart 420 involve normalizing the production values, determining the rate constants for production rate, and extracting the kinetic parameters from a plot of rate constants versus temperature.

FIGS. 15-19 show examples of graphical representations of successive steps to obtain the kinetic parameters as explained in the steps of flow chart 420. The kinetic parameters are obtained based on a set of simulated production data as can be generated using the described pyrolysis systems and methods.

Figure 15:
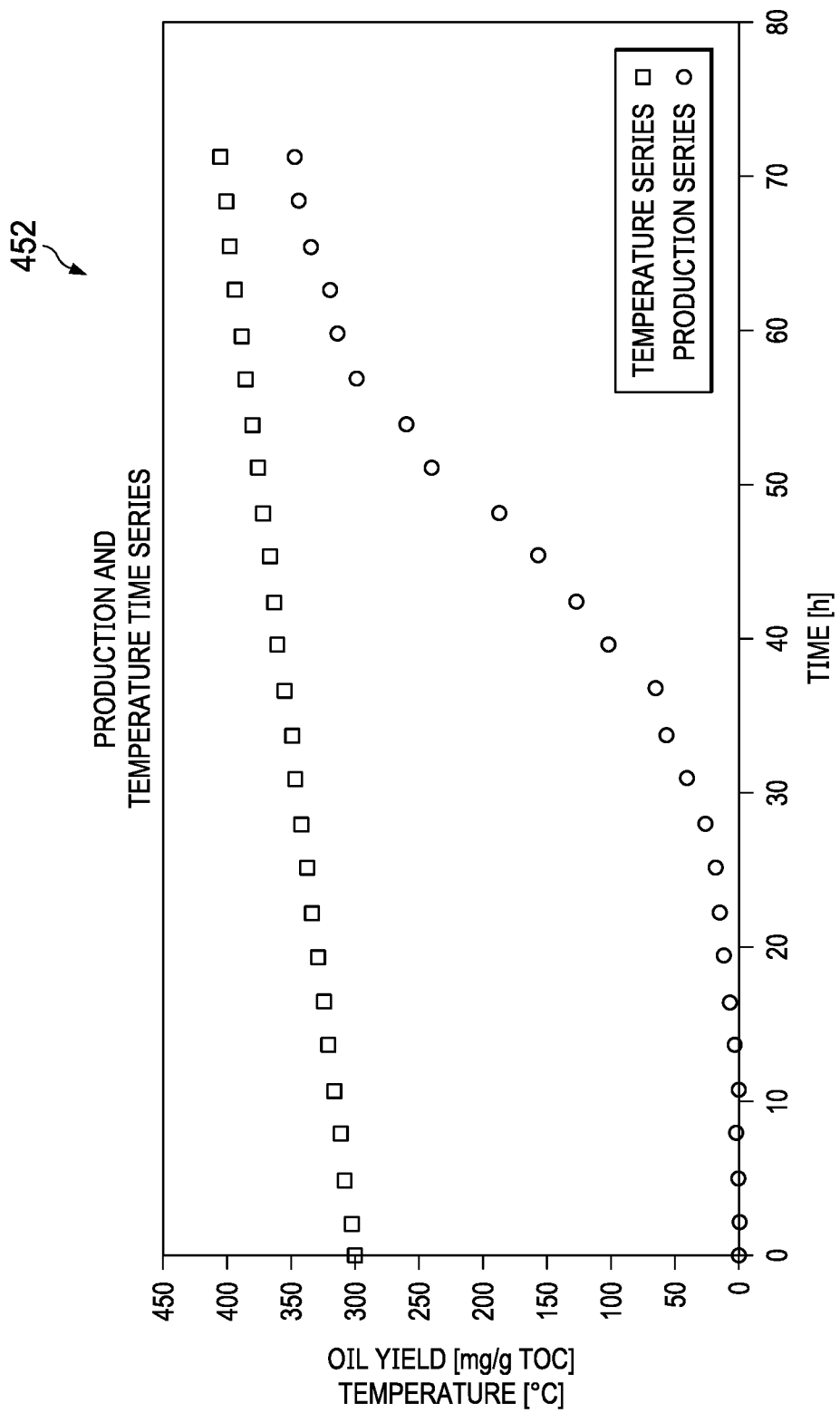
FIG. 15 is an example chart showing a plurality of time series production values obtained with direct sensor assembly.
Figure 16:
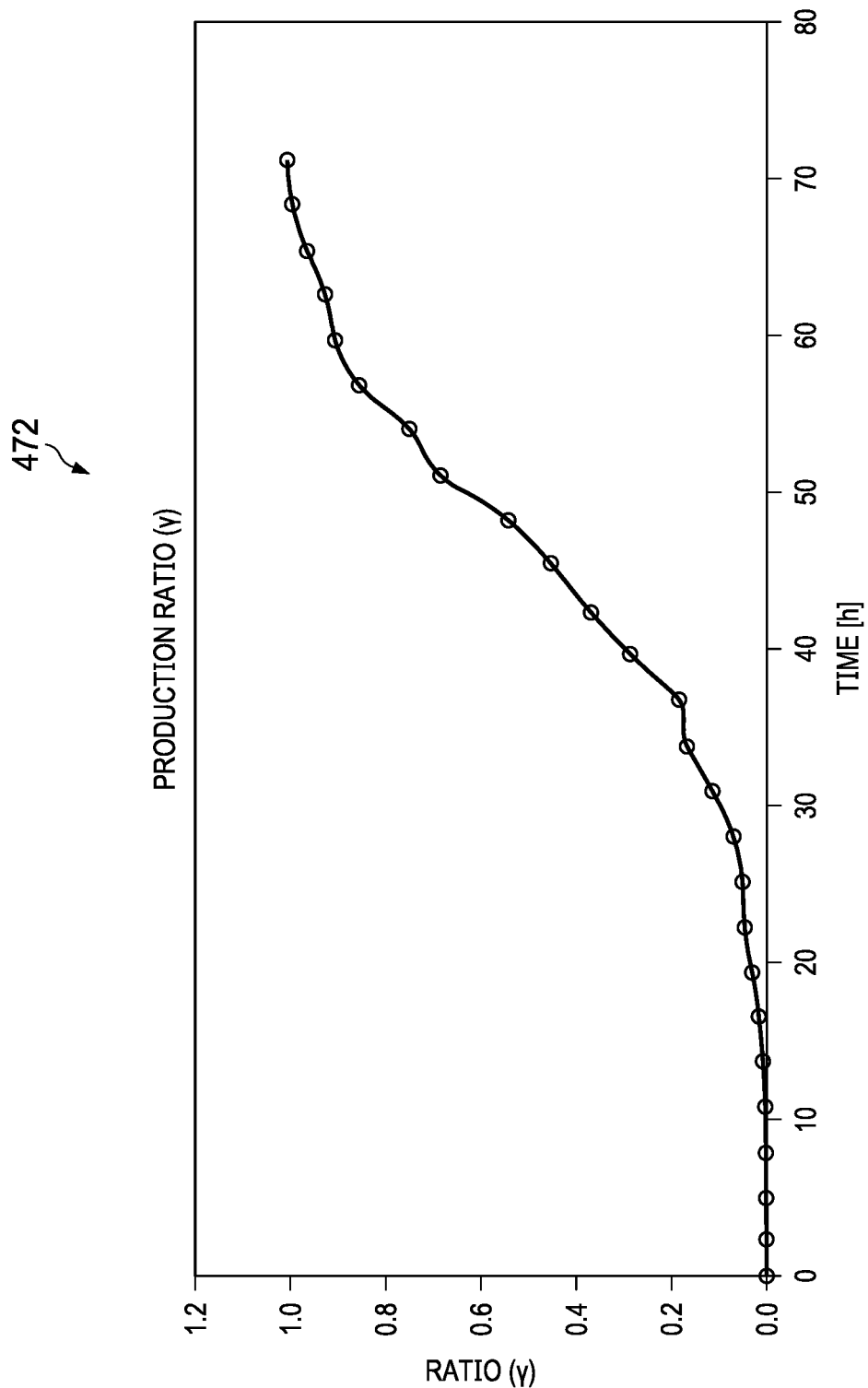
FIG. 16 is an example chart showing a calculated production ratio for a hydrocarbon component.
Figure 17:
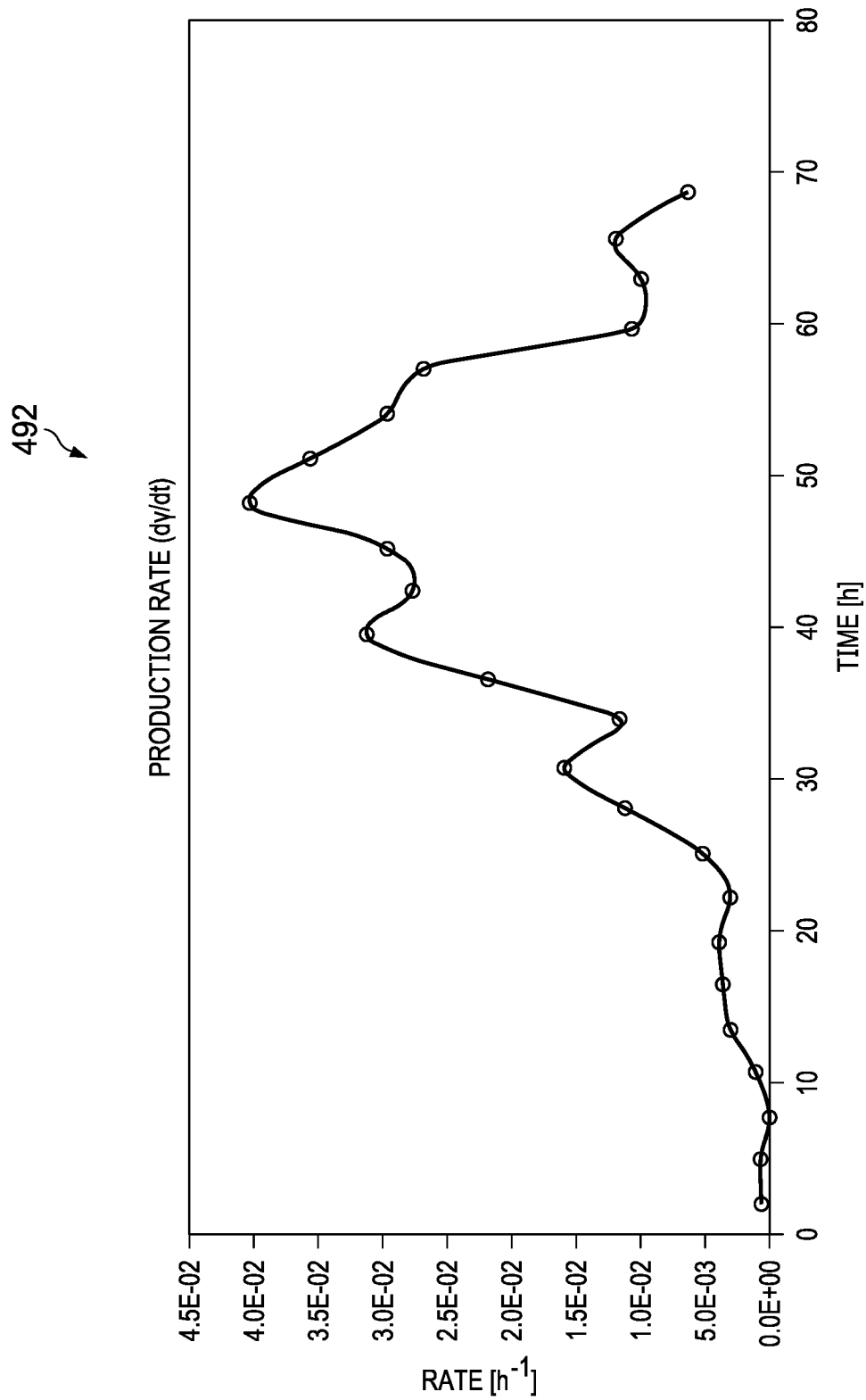
FIG. 17 is an example chart showing a calculated production rate from the production ratio chart in FIG. 16.
Figure 18:
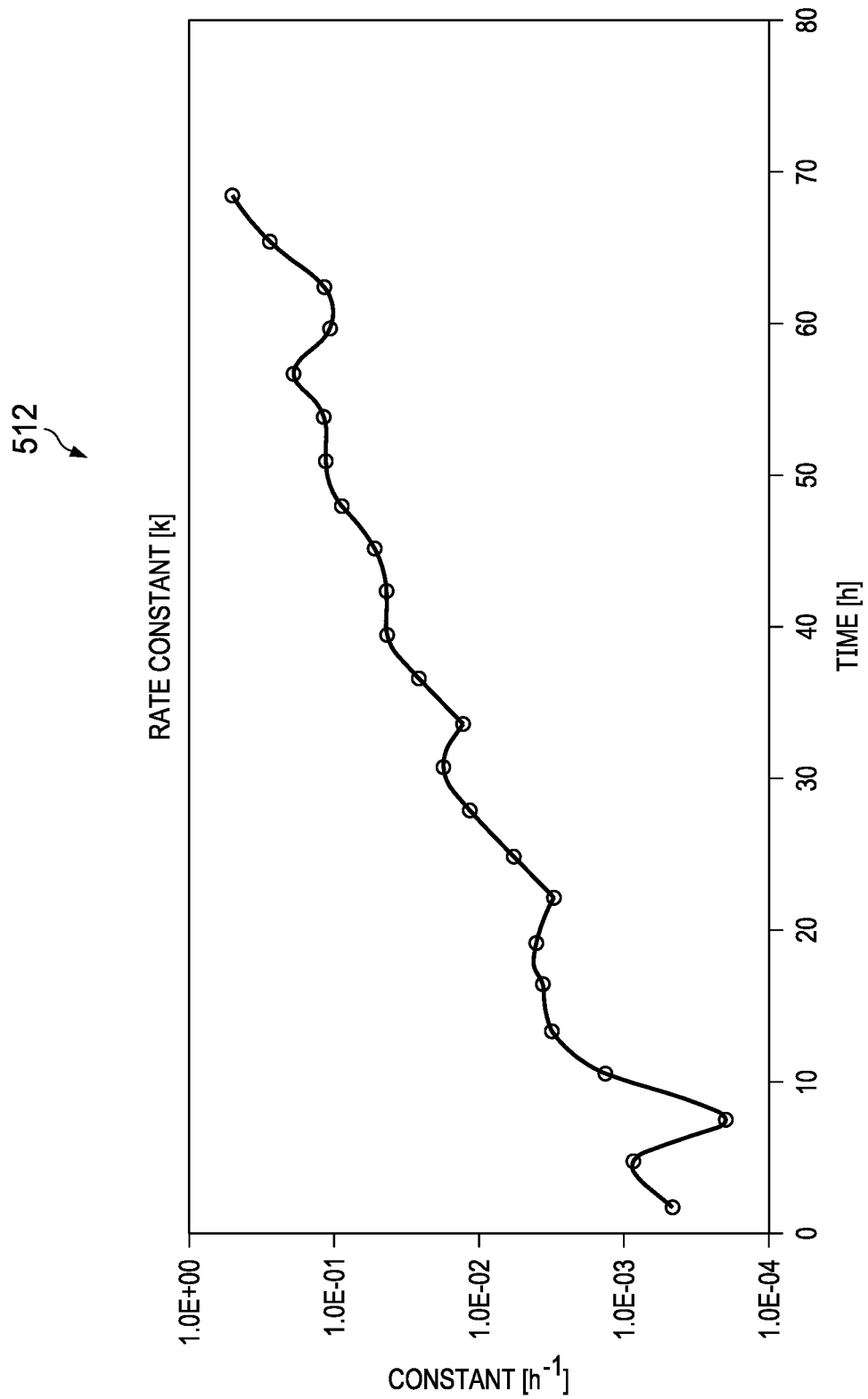
FIG. 18 is an example chart showing a constant rate for hydrocarbon component generation.
Figure 19:
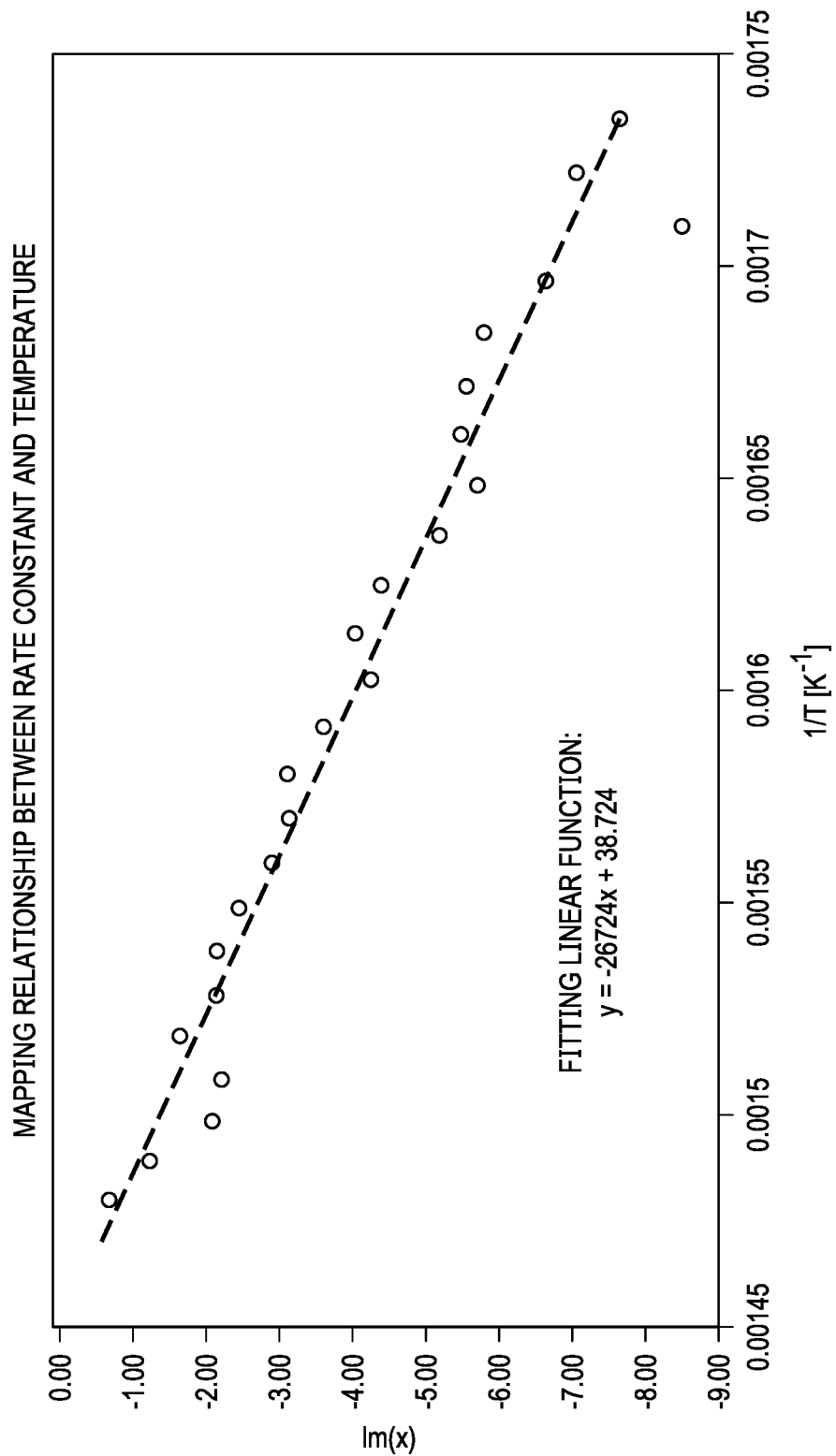
FIG. 19 is an example chart showing a relationship between a constant rate and a temperature.

FIG. 15 is an example chart 452 showing a plurality of time series production values obtained with direct sensor assembly. The production data is then normalized to total production value to obtain a production ratio at each time step. FIG. 16 is an example chart 472 showing a calculated production ratio for a hydrocarbon component. The normalized production data is used to obtain the production rate at each time step. FIG. 17 is an example chart 492 showing a calculated production rate from the production ratio chart in FIG. 16. The production rate can be extracted by interpolating a first derivative of the normalized production trend. From the first-order rate law of the chemical reaction that converts the original organic matter into a hydrocarbon component, a rate constant can be extracted by solving the differential equation relating the production rate to the production value. FIG. 18 is an example chart 512 showing a constant rate for hydrocarbon component generation. The kinetic parameters represent the equivalent activation energy (Ea) kcal/mol and frequency factor (A) $h^{-1}$ and are obtained from the slope and intercept of a linear fit line that best matches the mapping relationship between the reaction rate and the reaction temperature. FIG. 19 is an example chart 532 showing a relationship between a constant rate and a temperature and calculated using Equation 7:

$$k(T) = A \cdot \exp[-E_a/(R \cdot T)] \to \operatorname{Ln}(k(T)) = \operatorname{Ln}(A) - E_a/(R \cdot T) \qquad \text{Eq. (7)}$$

where T is the reaction temperature, R is the universal gas constant (8.31446 $J \cdot K^{-1} \cdot mol^{-1}$), A is a frequency factor, $E_a$ is the equivalent activation energy. A linear curve fit for the plotted points Ln (k (T)) to 1/T is calculated using Equation 8:

$$y(x) = a + b(x) \qquad \text{Eq. (8)}$$

with intercept a=Ln (A) and slope b=$-E_a/R$, a represents the oil saturation ratio within the sample under evaluation and b represents the measured resistivity in ohms-meters ($\Omega \cdot m$).

In some implementations, the described configuration of the pyrolysis system can be modified. For example, in addition to the measurements obtained from the source rock sample, the reactor vessel may include elements to obtain measurements from the generated hydrocarbon and nonhydrocarbon fluid components. For example, measurements from the fluid components can be collected by an inverted funnel system and directed to a marked column outside the reactor vessel. After phase separation, the progress of the generation process may be observed and recorded by an operator or by a specialized device that reads the fluids level and transmits the recorded data to the DAPS. In other examples, for very small volumes of fluids, an in-line detection method such as absorbance, fluorescence, infrared, Raman spectroscopy, or other similar methods to detect low hydrocarbon concentrations can be used. Similarly, mass spectrometry (MS), gas chromatography MS, and inductively coupled plasma (ICP) MS could be used as in-line or on small aliquots of the production fluids, hydrocarbons, and aqueous, to detect changes in the organic composition and aqueous composition. For example, ICP-MS can be used to detect changes in the salinity or trace ions that are released from the source rock sample. The recorded data can be converted into volume and mass of hydrocarbons generated based on the marked column specifications and recorded along with the time of reading or with the temperature value inside the reactor vessel. In another example, the time series may be correlated with real-time information from the source rock sample to obtain derived characteristics of the source rock such as generation kinetics, maturity indicators, source richness, or combinations thereof.

Figure 20:
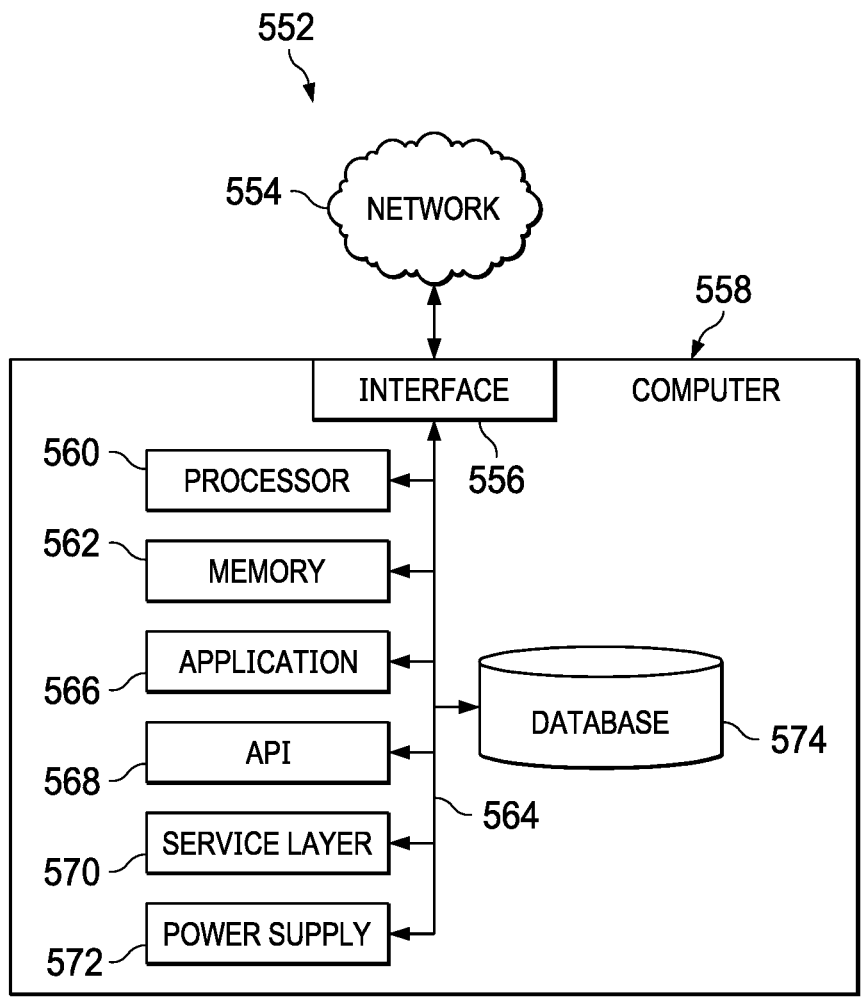
FIG. 20 is a block diagram of an example computer system.

FIG. 20 is a block diagram of an example computer system 552 used to provide computational functionalities associated with described algorithms, methods, functions, processes, flows, and procedures described in the present disclosure, according to some implementations of the present disclosure. The illustrated computer 558 is intended to encompass any computing device such as a server, a desktop computer, a laptop/notebook computer, a wireless data port, a smartphone, a personal data assistant (PDA), a tablet computing device, or one or more processors within these devices, including physical instances, virtual instances, or both. The computer 558 can include input devices such as keypads, keyboards, and touch screens that can accept user information. Also, the computer 558 can include output devices that can convey information associated with the operation of the computer 558 The information can include digital data, visual data, audio information, or a combination of information. The information can be presented in a graphical user interface (UI) (or GUI).

The computer 558 can serve in a role as a client, a network component, a server, a database, a persistency, or components of a computer system for performing the subject matter described in the present disclosure. The illustrated computer 558 is communicably coupled with a network 554. In some implementations, one or more components of the computer 558 can be configured to operate within different environments, including cloud-computing-based environments, local environments, global environments, and combinations of environments.

At a high level, the computer 558 is an electronic computing device operable to receive, transmit, process, store, and manage data and information associated with the described subject matter. According to some implementations, the computer 558 can also include, or be communicably coupled with, an application server, an email server, a web server, a caching server, a streaming data server, or a combination of servers.

The computer 558 can receive requests over network 554 from a client application (for example, executing on another computer 558). The computer 558 can respond to the received requests by processing the received requests using software applications. Requests can also be sent to the computer 558 from internal users (for example, from a command console), external (or third) parties, automated applications, entities, individuals, systems, and computers. Each of the components of the computer 558 can communicate using a system bus 564. In some implementations, any or all of the components of the computer 558, including hardware or software components, can interface with each other or the interface 556 (or a combination of both), over the system bus 564. Interfaces can use an application programming interface (API) 568, a service layer 570, or a combination of the API 568 and service layer 570. The API 568 can include specifications for routines, data structures, and object classes. The API 568 can be either computer-language independent or dependent. The API 568 can refer to a complete interface, a single function, or a set of APIs.

The service layer 570 can provide software services to the computer 558 and other components (whether illustrated or not) that are communicably coupled to the computer 558. The functionality of the computer 558 can be accessible for all service consumers using this service layer. Software services, such as those provided by the service layer 570, can provide reusable, defined functionalities through a defined interface. For example, the interface can be software written in JAVA, C++, or a language providing data in extensible markup language (XML) format. While illustrated as an integrated component of the computer 558, in alternative implementations, the API 568 or the service layer 570 can be stand-alone components in relation to other components of the computer 558 and other components communicably coupled to the computer 558. Moreover, any or all parts of the API 568 or the service layer 570 can be implemented as child or sub-modules of another software module, enterprise application, or hardware module without departing from the scope of the present disclosure.

The computer 558 includes an interface 556. Although illustrated as a single interface 556 in FIG. 10, two or more interfaces 556 can be used according to particular needs, desires, or particular implementations of the computer 558 and the described functionality. The interface 556 can be used by the computer 558 for communicating with other systems that are connected to the network 554 (whether illustrated or not) in a distributed environment. Generally, the interface 556 can include, or be implemented using, logic encoded in software or hardware (or a combination of software and hardware) operable to communicate with the network 554. More specifically, the interface 556 can include software supporting one or more communication protocols associated with communications. As such, the network 554 or the interface's hardware can be operable to communicate physical signals within and outside of the illustrated computer 558.

The computer 558 includes a processor 560. Although illustrated as a single processor 560 in FIG. 10, two or more processors 560 can be used according to particular needs, desires, or particular implementations of the computer 558 and the described functionality. Generally, the processor 560 can execute instructions and can manipulate data to perform the operations of the computer 558, including operations using algorithms, methods, functions, processes, flows, and procedures as described in the present disclosure.

The computer 558 also includes a database 574 that can hold data for the computer 558 and other components connected to the network 554 (whether illustrated or not). For example, database 574 can be an in-memory, conventional, or a database storing data consistent with the present disclosure. In some implementations, database 574 can be a combination of two or more different database types (for example, hybrid in-memory and conventional databases) according to particular needs, desires, or particular implementations of the computer 558 and the described functionality. Although illustrated as a single database 574 in FIG. 10, two or more databases (of the same, different, or combination of types) can be used according to particular needs, desires, or particular implementations of the computer 558 and the described functionality. While database 574 is illustrated as an internal component of the computer 558, in alternative implementations, database 574 can be external to the computer 558.

The computer 558 also includes a memory 562 that can hold data for the computer 558 or a combination of components connected to the network 554 (whether illustrated or not). Memory 562 can store any data consistent with the present disclosure. In some implementations, memory 562 can be a combination of two or more different types of memory (for example, a combination of semiconductor and magnetic storage) according to particular needs, desires, or particular implementations of the computer 558 and the described functionality. Although illustrated as a single memory 562 in FIG. 10, two or more memories 562 (of the same, different, or combination of types) can be used according to particular needs, desires, or particular implementations of the computer 558 and the described functionality. While memory 562 is illustrated as an internal component of the computer 558, in alternative implementations, memory 562 can be external to the computer 558.

The application 566 can be an algorithmic software engine providing functionality according to particular needs, desires, or particular implementations of the computer 558 and the described functionality. For example, application 566 can serve as one or more components, modules, or applications. Further, although illustrated as a single application 566, the application 566 can be implemented as multiple applications 566 on the computer 558. In addition, although illustrated as internal to the computer 558, in alternative implementations, the application 566 can be external to the computer 558.

The computer 558 can also include a power supply 572. The power supply 572 can include a rechargeable or non-rechargeable battery that can be configured to be either user- or non-user-replaceable. In some implementations, the power supply 572 can include power-conversion and management circuits, including recharging, standby, and power management functionalities. In some implementations, the power-supply 572 can include a power plug to allow the computer 558 to be plugged into a wall socket or a power source to, for example, power the computer 558 or recharge a rechargeable battery.

There can be any number of computers 558 associated with, or external to, a computer system containing computer 558, with each computer 558 communicating over network 554. Further, the terms "client," "user," and other appropriate terminology can be used interchangeably, as appropriate, without departing from the scope of the present disclosure.

Moreover, the present disclosure contemplates that many users can use one computer 558 and one user can use multiple computers 558.

Implementations of the subject matter and the functional operations described in this specification can be implemented in digital electronic circuitry, intangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially-generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure. Accordingly, other embodiments are within the scope of the following claims.

What is claimed is:

1. A pyrolysis system for evaluating a source rock sample from a subterranean reservoir, the pyrolysis system comprising:

a reactor vessel comprising a body with an open end, a cover attachable to the open end of the body, a heating system, and a collector assembly, wherein the body and the cover define a sealable chamber, and wherein the collector assembly comprises an oil section, a gas section, and a measurement tool comprising a ruled level scale for the oil section and the gas section;

a source rock sample holder sized to be received inside the sealable chamber; and a sensor system comprising:

a direct sensor assembly associated with the source rock sample holder, sized to be received inside the sealable chamber, and operable to measure properties of the source rock sample in the source rock sample holder; and a pyrolysis products sensor assembly in fluid communication with the collector assembly of the reactor vessel, wherein the direct sensor assembly comprises an acoustic travel time (ATT) sensor comprising a geophone and an acoustic source.

2. The system of claim 1, wherein the direct sensor assembly is attached to or part of the source rock sample holder.

3. The system of claim 1, wherein the acoustic travel time (ATT) sensor is operable to measure a length of time it takes a sound signal to travel through the source rock sample.

4. The system of claim 1, wherein the heating system comprises a heating coil incorporated in walls of the reactor vessel.

5. The system of claim 4, wherein the heating system comprises a thermal controller in electronic communication with the heating coil.

6. The system of claim 5, wherein the heating system comprises a temperature probe in electronic communication with the thermal controller.

7. The system of claim 1, further comprising a pressure control system inlet comprising a pressure gauge configured to measure a pressure inside the sealable chamber.

8. The system of claim 1, wherein the sensor system is in electronic communication with a data acquisition and processing system (DAPS).

9. A method for evaluating a source rock sample of a subterranean reservoir, the method comprising:

loading the source rock sample into a source rock sample holder sized to be received inside a sealable chamber of a reactor vessel;

sealing the source rock sample inside the sealable chamber;

controlling a temperature of the sealable chamber to perform pyrolysis of the source rock sample;

collecting pyrolysis products from the source rock sample while controlling the temperature of the sealable chamber;

separating the pyrolysis products into a gas section and an oil section of a collector assembly of the reactor vessel;

measuring a level of the pyrolysis products in the gas section and the oil section using a measurement tool comprising a ruled level scale;

measuring a plurality of time-series of properties of the pyrolysis products using a pyrolysis products sensor assembly while controlling the temperature of the sealable chamber;

measuring a plurality of time-series of properties of the source rock sample using a direct sensor assembly while controlling the temperature of the sealable chamber; and determining a plurality of kinetic parameters based on the plurality of time-series of properties of the pyrolysis products and based on the plurality of time-series of properties of the source rock sample, wherein measuring a plurality of time-series of properties of the source rock sample comprises measuring a length of time for a sound signal to travel through the source rock sample using an acoustic travel time sensor comprising a geophone and an acoustic source.

10. The method of claim 9, further comprising partially filling a volume with a liquid solution, wherein an inside space of the sealable chamber defines the volume.

11. The method of claim 10, further comprising transferring with the liquid solution a plurality of generated products from the source rock sample to the collector assembly.

12. The method of claim 11, further comprising monitoring and sampling the plurality of generated products from the source rock sample with the collector assembly.

13. The method of claim 10, further comprising transferring heat from a heating system to the source rock sample.

14. The method of claim 9, further comprising processing the plurality of time-series of properties from the source rock sample using a data acquisition and processing system (DAPS).

15. The method of claim 9, further comprising acquiring the plurality of time-series of properties from the source rock sample by measuring an electrical resistivity of the source rock sample.

16. The method of claim 9, further comprising acquiring the plurality of time-series of properties from the source rock sample by measuring a length of time it takes a sound signal to travel through the source rock sample.

17. The method of claim 9, further comprising acquiring the plurality of time-series of properties from the source rock sample by measuring a radio frequency (RF) signal produced within the source rock sample.

* * * * *